US007964743B2

(12) United States Patent
Miyaura et al.

(10) Patent No.: US 7,964,743 B2
(45) Date of Patent: Jun. 21, 2011

(54) CATALYST FOR ASYMMETRIC SYNTHESIS, LIGAND FOR USE THEREIN, AND PROCESS FOR PRODUCING OPTICALLY ACTIVE COMPOUND THROUGH ASYMMETRIC SYNTHESIS REACTION USING THEM

(75) Inventors: Norio Miyaura, Sapporo (JP); Yasunori Yamamoto, Sapporo (JP)

(73) Assignee: Japan Science and Technology Agency, Saitama (JP)

( * ) Notice: Subject to any disclaimer, the term of this patent is extended or adjusted under 35 U.S.C. 154(b) by 557 days.

(21) Appl. No.: 11/884,537

(22) PCT Filed: Feb. 17, 2006

(86) PCT No.: PCT/JP2006/302850
§ 371 (c)(1),
(2), (4) Date: May 23, 2008

(87) PCT Pub. No.: WO2006/088142
PCT Pub. Date: Aug. 24, 2006

(65) Prior Publication Data
US 2009/0156849 A1    Jun. 18, 2009

(30) Foreign Application Priority Data

Feb. 17, 2005  (JP) ................................. 2005-041116

(51) Int. Cl.
*C07F 15/00*  (2006.01)
*C07F 9/00*  (2006.01)
(52) U.S. Cl. ............ 556/13; 562/595; 564/12; 564/468; 568/12; 568/700
(58) Field of Classification Search .................... 556/13; 562/595; 564/12, 468; 568/12, 700
See application file for complete search history.

(56) References Cited

U.S. PATENT DOCUMENTS
2004/0199023 A1   10/2004  Whiteker et al.

FOREIGN PATENT DOCUMENTS
JP           2004-315457      11/2004

OTHER PUBLICATIONS

XP002479576, Dieguez et al., "Asymmetric hydroformylation of styrene catalyzed by carbohydrate diphosphite-Rh(I) complexes", New J. Chem., vol. 26, No. 7, 2002, pp. 827-833.
XP008091272, Yamamoto et al., "Chiral bis-phosphoramidites based on linked-BINOL for rhodium-catalyzed 1,4-addition of arylboronic acids to . . . ", Chemistry letters, 34(9), 12241225.
Bähr, Anja et al., "Dendritic 1,1'-Binaphthalene-Derived Cleft-Type Receptors (*Dendroclefts*) for the Molecular Recognition of Pyranosides," Helvetica Chimica Acta, 2000, 83 (7), pp. 1346-1376.
Korostylev, Andrei et al., "BINOL derived monodentate acylphosphite ligands for homogenously catalyed enantioselective hydrogenation," Tetrahedron: Asymmetry, 2004, 15 (6), pp. 1001-1005.

*Primary Examiner* — Porfirio Nazario Gonzalez
(74) *Attorney, Agent, or Firm* — Jacobson Holman PLLC

(57) ABSTRACT

Compounds represented by the following general formula (1a) or (1b).

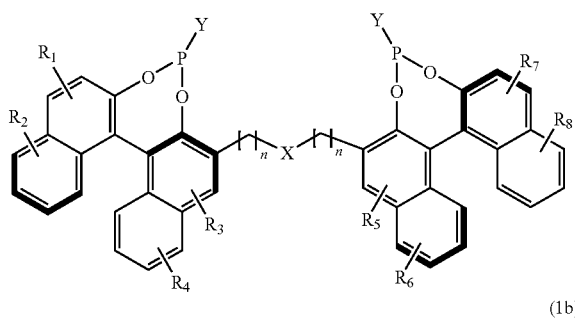

(1a)

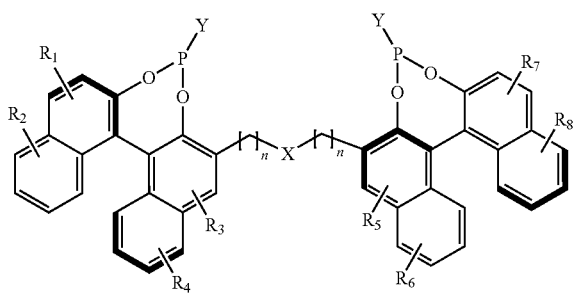

(1b)

A complex comprising a center metal of rhodium and a compound represented by the following general formula (1a) or (1b) as a ligand. A catalyst for optically active beta-substituted carbonyl compound synthesis and catalyst for asymmetric 1, 2 addition reaction being composed of the complex. A method of production of an optically active beta-aryl compound from an alpha, beta-unsaturated compound and an aryl-boronic acid derivative and method of production of an optically active aryl alcohol compound from an aldehyde compound and aryl boronic acid derivatives using the catalyst. A complex comprising a center metal of palladium and a compound represented by the following general formula (1a) or (1b) as a ligand. A catalyst for asymmetric allylic substitution reaction being composed of the complex. A method of production of an optically active dialkyl (1,3-disubstituted propeny)malonate compound from a 1,3-disubstituted ally acetate compound and a dialkyl malonate and method of production of an optically active allylamine compound from a 1,3-disubstituted ally acetate compound and an amine compound. The compounds have not only the versatility of being usable in the synthesis of wide-ranging optically active aryl compounds but also the selectivity and reactivity permitting synthesis with high yield within a short period of time under industrially advantageous mild conditions.

29 Claims, No Drawings

CATALYST FOR ASYMMETRIC SYNTHESIS, LIGAND FOR USE THEREIN, AND PROCESS FOR PRODUCING OPTICALLY ACTIVE COMPOUND THROUGH ASYMMETRIC SYNTHESIS REACTION USING THEM

This is a 371 of PCT/JP06/302850 filed Feb. 17, 2006.

TECHNICAL FIELD

The present invention relates to a catalyst for asymmetric synthesis, a ligand employed in the same, and a method of manufacturing optically active compounds by an asymmetric synthesis reaction employing the catalyst and ligand. More particularly, the method of manufacturing optically active compounds includes a method of manufacturing optically active beta-substituted carbonyl compounds, a method of manufacturing optically active alcohol compounds, and an allylic substitution reaction.

BACKGROUND ART

Optically active beta-substituted carbonyl compounds are employed as intermediates in the fields of pharmaceuticals, food additives, and the like. Examples of known methods of manufacturing beta-substituted carbonyl compounds are given below.

1) Methods of manufacturing linear or cyclic beta-substituted carbonyl compounds by reacting arylboronic acid and alpha, beta-unsaturated enones in the presence of a rhodium compound, a phosphine compound, and a base have been reported (*Tetrahedron Lett.*, 1998, 39, 8479; *J. Am. Chem. Soc.*, 2002, 124, 8932; *J. Am. Chem. Soc.*, 2003, 125, 1110, and the like).
2) A method of manufacturing optically active beta-arylamide compounds by reacting arylboronic acid and alpha, beta-unsaturated amide compounds in the presence of a rhodium compound and an optically active phosphine compound has been reported (*J. Org. Chem.*, 2001, 66, 8944).
3) A methods of manufacturing optically active beta-arylester compounds by reacting arylboronic acid and alpha, beta-unsaturated ester compounds in the presence of a rhodium compound and optically active phosphine compounds have been reported (*J. Am. Chem. Soc.*, 2002, 124, 5052).
4) The obtaining of a desired optically active beta-aryl compound by adding a base in the presence of a rhodium complex produced from a rhodium compound and an optically active phosphine compound has been reported (Japanese Unexamined Patent Publication (KOKAI) No. 2004-315396).
5) The obtaining of an optically active aryl compound by the asymmetric 1,2-addition reaction of an aldehyde and arylboronic acid in the presence of a rhodium catalyst has been reported (*Angew. Chem. Int. Ed.* 1998, 37, 3279-3281).

DESCRIPTION OF THE INVENTION

However, in the manufacturing methods of 1) and 2) above, an extended reaction must be conducted at an elevated reaction temperature of 90 to 100° C., tending to result in problems such as reduced yield and a reduced optical yield due to side reactions. Although the reaction in 3) is conducted at about 35° C., there are limits in the types of substrates that can be employed, which is disadvantageous to the synthesis of desired intermediates in industrial manufacturing. Although a desired optically active beta-aryl compound can be obtained under mild reaction conditions in 4), the yield and optical purity of the optically active beta-aryl compound obtained are inadequate, leaving room for improvement. There is also a problem in that the reaction application range is narrow. In 5), there are problems in that the yield of optically active aryl compound is low and selectivity is poor as well.

That is, the development of a manufacturing method that can be broadly applied to the rapid synthesis of optically active aryl compounds under industrially advantageous mild conditions, combining both reactivity and selectivity permitting synthesis at high yields, has become a problem to be solved in this field.

[Means of Solving the Problem]

The present inventors conducted extensive research into solving the above-stated problem. As a result, they discovered that when reacting alpha, beta-unsaturated compounds with arylboronic acid derivatives, the use of a rhodium catalyst with a bidentate phosphoramidite compound as ligand produced the desired optically active beta-aryl compounds at high yield and with high optical purity; the present invention was devised on this basis.

They also discovered that in reactions producing an optically active aryl alcohol compound by reacting an aldehyde compound and an arylboronic acid derivative, the desired optically active aryl compound was obtained at high yield and with high optical purity using a rhodium catalyst with a bidentate phosphoramidite compound as ligand.

They further discovered that in methods for manufacturing optically active allylamine compounds and optical active (1,3-disubstituted propenyl)dialkyl malonate compounds by an asymmetric allylic substitution reaction employing a palladium catalyst with the above-described bidentate phosphoramidite compound as ligand, the desired optically active allylic compounds were obtained at high yield and with high optical purity.

The present invention solves the above-stated problem as follows:

[1]

A compound denoted by general formula (1a) or (1b) below:

[Chem. 1]

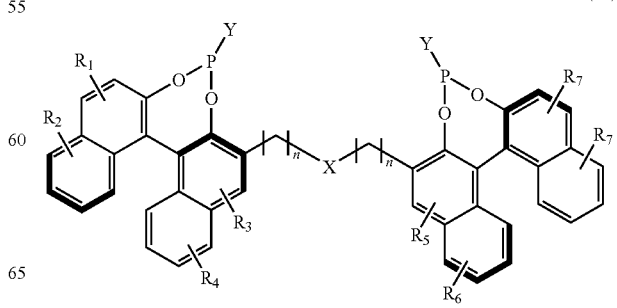

(1a)

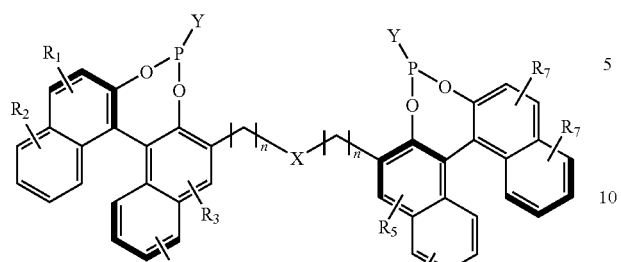

(1b)

(wherein X denotes carbon, oxygen, sulfur, or nitrogen; Y denotes $NR^{10}R^{11}$ (wherein $R^{10}$ and $R^{11}$ each independently denote a substituted or unsubstituted alkyl group, or a substituted or unsubstituted aryl group), $OR^{12}$ (wherein $R^{12}$ denotes a substituted or unsubstituted alkyl group, or substituted or unsubstituted aryl group), or $SR^{13}$ (wherein $R^{13}$ denotes a substituted or unsubstituted alkyl group, or a substituted or unsubstituted aryl group); n denotes an integer of from 1 to 3; $R^1$ to $R^8$ each independently denote hydrogen, a substituted or unsubstituted alkyl group, or a substituted or unsubstituted aryl group).

[2]

A complex, the core metal of which is rhodium, iridium, or ruthenium, comprising the compound denoted by general formula (1a) or (1b) of [1] as ligand.

[3]

The complex according to [2] denoted by general formula (20) below:

$$M^1 X_m L^1_p L^2_q \quad (20)$$

(wherein $M^1$ denotes rhodium, iridium, or ruthenium; X denotes a halogen, RO (wherein RO denotes a member selected from the group consisting of hydroxy, alkoxy, acetyl acetonate, acetoxy, and trifluoromethane sulfonate), a $BF_4$, $ClO_4$, $PF_6$, $B(Ar)_4$, or $SbF_6$ anion, or hydrogen; m denotes an integer of from 1 to 3; $L^1$ denotes an olefin, $eta^3$-allyl, aryl (Ar) group, amine, carbon monoxide, or acetonitrile; p denotes an integer of from 0 to 3; $L^2$ denotes the compound represented by general formula (1a) or (1b) in [1]; q denotes the integer 1 or 2; and aryl (Ar) denotes an aromatic ring).

[4]

A catalyst for synthesizing optically active beta-substituted carbonyl compounds comprising the complexes according to [2] and [3].

[5]

A catalyst for asymmetric 1,2-addition reactions comprised of the complexes according to [2] and [3].

[6]

A method of manufacturing an optically active beta-substituted carbonyl compound by reacting a substituted or unsubstituted alpha, beta-unsaturated compound and an organometallic reagent, characterized by conducting the reaction in the presence of the complex according to [2] or [3].

[7]

The method according to [6] wherein the substituent in said alpha, beta-unsaturated compound is a carboxyl group, alkoxycarbonyl group, cyano group, substituted carbamoyl group, acyl group, formyl group, or nitro group.

[8]

The method according to [6] wherein said alpha, beta-unsaturated compound is a compound denoted by general formula (2a) or (2b) below:

[Chem. 2]

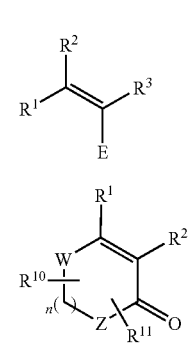

(2a)

(2b)

(wherein $R^1$, $R^2$, and $R^3$, which may be identical or different, each denote a hydrogen, alkyl group having 1 to 8 carbon atoms, alkoxy group having 1 to 8 carbon atoms, alkylthio group having 1 to 8 carbon atoms, or amino group optionally having an alkyl group with 1 to 8 carbon atoms; E denotes a carboxyl group, cyano group, carbamoyl group optionally having an alkyl group with 1 to 8 carbon atoms, or nitro group; n denotes an integer of 0 or greater; W and Z, which may be identical or different, each denote $—CH_2—$, $=CH—$, $—O—$, $—S—$, $—NH—$, or $=N—$; $R^{10}$ and $R^{11}$, which may be identical or different, each denote a hydrogen atom, alkyl group having 1 to 8 carbon atoms, alkoxy group having 1 to 8 carbon atoms, nitro group, cyano group, acyl group having 2 to 8 carbon atoms, alkoxycarbonyl group having 2 to 8 carbon atoms, or amino group optionally having an alkyl group with 1 to 8 carbon atoms, or adjacent $R^{10}$ and $R^{11}$ denote general formula (a) below:

[Chem. 3]

(a)

(wherein $R^{12}$ denotes a hydrogen atom, alkyl group having 1 to 8 carbon atoms, alkoxy group having 1 to 8 carbon atoms, cyano group, halogenated alkyl group, halogen atom, carbamoyl group optionally having an alkyl group with 1 to 8 carbon atoms, acyl group having 2 to 8 carbon atoms, alkoxycarbonyl group having 2 to 8 carbon atoms, or amino group optionally having an alkyl group with 1 to 8 carbon atoms)).

[9]

The method according to any one of [6] to [8], wherein said metal reagent is a metal-substituted or unsubstituted alkyl, alkenyl, alkynyl, or aryl groups.

[10]

The method according to any one of [6] to [8] wherein said metal reagent is an organoboronic acid derivative of the compound denoted by general formula (3a), (3b), or (3c):

[Chem. 4]

(3a)

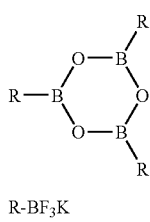
(3b)

R-BF$_3$K (3c)

(wherein Y denotes a hydroxyl group, alkoxy group having 1 to 8 carbon atoms, phenoxy group optionally having an alkyl group with 1 to 8 carbon atoms, cyclohexyloxy group, or group denoted by formula a, b, c, or d (in each of which q denotes an integer of from 1 to 4; r and s each independently denote an integer of from 0 to 5, and Me denotes a methyl group); and R denotes a substituted or unsubstituted alkyl, alkenyl, alkynyl, or aryl group).

[Chem. 5]

 a

 b

 c

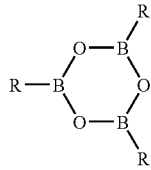 d

[11]
The method according to any of [6] to [10] wherein said optically active beta-substituted carbonyl compound denotes the compound represented by general formula (4) below:

[Chem. 6]

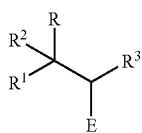
(4)

(wherein R$^1$, R$^2$, and R$^3$, which may be identical or different, each denote a hydrogen atom, alkyl group having 1 to 8 carbon atoms, alkoxy group having 1 to 8 carbon atoms, alkylthio group having 1 to 8 carbon atoms, or amino group optionally having an alkyl group with 1 to 8 carbon atoms; E denotes a carboxyl group, cyano group, carbamoyl group optionally having an alkyl group with 1 to 8 carbon atoms, or nitro group; and R denotes a substituted or unsubstituted alkyl, alkenyl, alkynyl, or aryl group).

[12]
A method of manufacturing an optically active alcohol compound by reacting an aldehyde compound and an organometallic reagent, characterized by being conducted in the presence of the complex according to [2] or [3].

[13]
The method according to [12], wherein said aldehyde compound is the compound denoted by general formula (5):

R$^4$CHO (5)

(wherein R$^4$ denotes a substituted or unsubstituted alkyl group or substituted or unsubstituted aryl group).

[14]
The method according to [12] or [13], wherein said metal reagent is a metal-substituted or unsubstituted alkyl, alkenyl, alkynyl, or aryl group.

[15]
The method according to [12] or [13], wherein said metal reagent is an organic boronic acid derivative denoted by general formula (3a), (3b), or (3c) below:

[Chem. 7]

(3a)

(3b)

R-BF$_3$K (3c)

(wherein Y denotes a hydroxyl group, alkoxy group having 1 to 8 carbon atoms, phenoxy group optionally having an alkyl group with 1 to 8 carbon atoms, cyclohexyloxy group, or the group denoted by formula a, b, c, or d below (in each of which q denotes an integer of from 1 to 4, r and s each independently denote an integer of from 0 to 5, and Me denotes a methyl group); and R denotes a substituted or unsubstituted alkyl, alkenyl, alkynyl, or aryl group):

[Chem. 8]

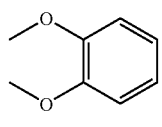 a

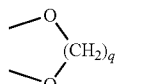 b

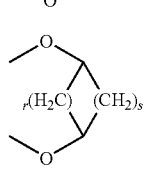 c

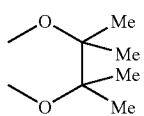

d

[16]

The method according to any of [12] to [15], wherein said optically active alcohol is the compound denoted by general formula (7) below:

[Chem. 9]

(7)

(wherein $R^4$ denotes a substituted or unsubstituted alkyl group or a substituted or unsubstituted aryl group; and R denotes a substituted or unsubstituted alkyl, alkenyl, alkynyl, or aryl group).

[17]

A complex, the core metal of which is palladium or platinum, comprising the compound denoted by general formula (1a) or (1b) of [1] as ligand.

[18]

The complex according to [17], denoted by general formula (21) below:

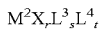 (21)

(wherein $M^2$ denotes palladium or platinum; X denotes a halogen, acetate anion, $BF_4$, $PF_6$, $ClO_4$, $B(Ar)_4$, or $SbF_6$ anion; r denotes an integer of from 0 to 2; $L^3$ denotes a triaryl (or alkyl) phosphine, acetonitrile, benzonitrile, dibenzylidene acetone, or eta$^3$-allyl; s denotes an integer of from 0 to 2; $L^4$ denotes the compound according to general formula (1a) or (1b) in [1]; t denotes 1; and Ar denotes an aromatic ring).

[19]

A catalyst for an asymmetric allylic substitution reaction, comprising the complex according to [17] or [18].

[20]

The catalyst according to [19], in which the asymmetric allylic substitution reaction is an asymmetric allylic alkylation reaction.

[21]

The catalyst according to [19], wherein the asymmetric allylic substitution reaction is an asymmetric allylic amination reaction.

[22]

A method of manufacturing an optically active (1,3-disubstituted propenyl)dialkyl malonate compound by reacting a 1,3-disubstituted allyl acetate compound with a dialkyl malonate, characterized by conducting said reaction in the presence of the complex according to [17] or [18].

[23]

The method according to [22], wherein said 1,3-disubstituted allyl acetate compound is the compound denoted by general formula (8) below:

[Chem. 10]

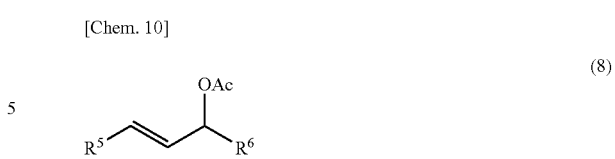

(8)

(wherein $R^5$ and $R^6$ denote identical substituted or unsubstituted alkyl groups, or substituted or unsubstituted aryl groups; and Ac denotes an acetyl group).

[24]

The method according to [22] or [23], wherein said dialkyl malonate is the compound dented by general formula (9) below:

[Chem. 11]

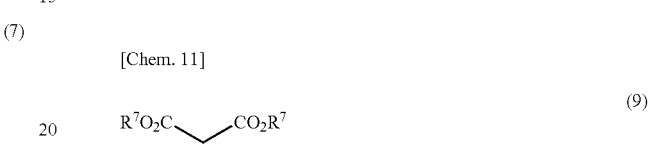

(9)

(wherein $R^7$ denotes a substituted or unsubstituted alkyl group).

[25]

The method according to any one of [22] to [24], wherein said optically active (1,3-disubstituted propenyl)dialkyl malonate compound is the compound denoted by general formula (10) below:

[Chem. 12]

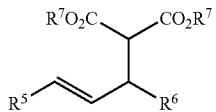

(10)

(wherein $R^5$ and $R^6$ denote identical substituted or unsubstituted alkyl groups or substituted or unsubstituted aryl groups; and $R^7$ denotes a substituted or unsubstituted alkyl group).

[26]

A method of manufacturing an optically active allylamine compound by reacting a 1,3-disubstituted allyl acetate compound and an amine compound, characterized by conducting said reaction in the presence of the complex according to [17] or [18].

[27]

The method according to [26], wherein said 1,3-disubstituted allyl acetate compound is the compound denoted by general formula (11) below:

[Chem. 13]

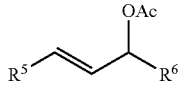

(11)

(wherein $R^5$ and $R^6$ denote identical substituted or unsubstituted alkyl groups or substituted or unsubstituted aryl groups; and Ac denotes an acetyl group).

[28]

The method according to [26] or [27], wherein said amine compound is the compound denoted by general formula (12) below:

[Chem. 14]

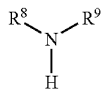

(12)

(wherein $R^8$ and $R^9$ each independently denote hydrogen, a substituted or unsubstituted alkyl group, or a substituted or unsubstituted aryl group, it being permissible for $R^8$ and $R^9$ to form a ring having 3 to 7 carbon atoms).

[29]

The method according to any one of [26] to [28], wherein said optically active allylamine compound is the compound denoted by general formula (13) below:

[Chem. 15]

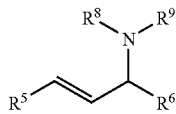

(13)

(wherein $R^5$ and $R^6$ denote identical substituted or unsubstituted alkyl groups or substituted or unsubstituted aryl groups; and $R^8$ and $R^9$ each independently denote hydrogen, a substituted or unsubstituted alkyl group, or a substituted or unsubstituted aryl group, it being permissible for $R^8$ and $R^9$ to form a ring having 3 to 7 carbon atoms).

[Advantages of the Invention]

According to the present invention, a rhodium catalyst having a bidentate phosphoramidite compound as ligand is provided when reacting an alpha, beta-unsaturated compound with an arylboronic acid derivative. Employing this catalyst, it is possible to obtain an optically active beta-aryl compound with high yield and high optical purity.

Further, a desired optically active aryl compound can be obtained at high yield and with high optical purity by a method for manufacturing an optically active aryl alcohol compound by reacting an aldehyde compound and an arylboronic acid derivative using the rhodium catalyst of the present invention having the above-described bidentate phosphoramidide compound as ligand.

Additionally, a desired optically active allyl compound can be obtained at high yield and with high optical purity by a method for manufacturing an optically active allylamine compound and a method for manufacturing an optically active (1,3-disubstituted propenyl)dialkyl malonate compound by an asymmetric allylic substitution reaction using the palladium catalyst of the present invention having the above-described bidentate phosphoramidite compound as ligand.

[Best Mode of Implementing the Invention]

[The Ligand]

The present invention relates to the compounds denoted by general formulas (1a) and (1b) below. These compounds are useful as the ligands of the catalysts described further below.

[Chem. 16]

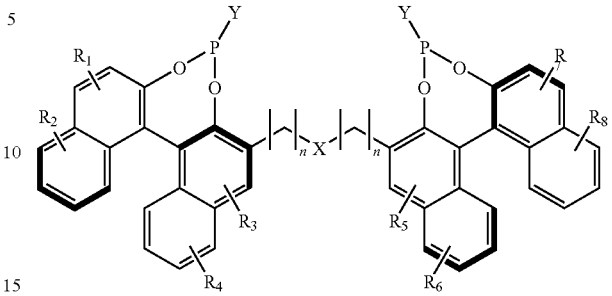

(1a)

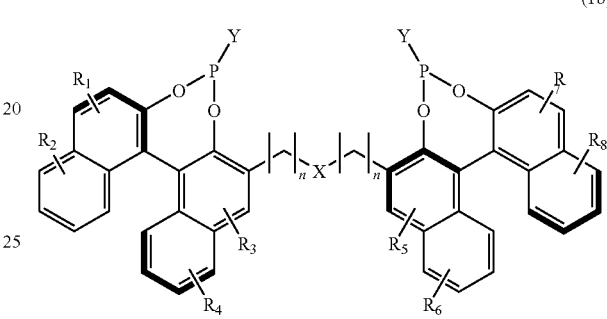

(1b)

In the formulas, X denotes carbon, oxygen, sulfur, or nitrogen, preferably oxygen.

Y denotes $NR^{10}R^{11}$, $OR^{12}$, or $SR^{13}$. In $NR^{10}R^{11}$, $R^{10}$ and $R^{11}$ each independently denote a substituted or unsubstituted alkyl group or substituted or unsubstituted aryl group. The alkyl group, by way of example, may have 1 to 8 carbon atoms; examples of substituents on the alkyl group or on the aryl group are alcohol, amine, carboxylic acid, ester, amide, ether, and acyl groups. $R^{10}$ and $R^{11}$ each desirably independently denote a linear or branching alkyl group, preferably a methyl group, ethyl group, or iso-propyl group.

In $OR^{12}$, $R^{12}$ denotes a substituted or unsubstituted alkyl group or a substituted or unsubstituted aryl group. The alkyl group, by way of example, may have 1 to 8 carbon atoms; examples of substituents on the alkyl group or on the aryl group are alcohol, amine, carboxylic acid, ester, amide, ether, and acyl groups. $R^{12}$ desirably denotes a substituted or unsubstituted phenyl group, preferably an unsubstituted phenyl group.

In $SR^{13}$, $R^{13}$ denotes a substituted or unsubstituted alkyl group or a substituted or unsubstituted aryl group. The alkyl group, by way of example, may have 1 to 8 carbon atoms; examples of substituents on the alkyl group or on the aryl group are alcohol, amine, carboxylic acid, ester, amide, ether, and acyl groups. $R^{13}$ desirably denotes a substituted or unsubstituted phenyl group, preferably an unsubstituted phenyl group.

n denotes an integer of from 1 to 3, desirably 1 or 2, and preferably, 1.

$R^1$ to $R^8$ each independently denote a hydrogen atom, a substituted or unsubstituted alkyl group, or a substituted or unsubstituted aryl group. Examples of substituents on the alkyl group or on the aryl group are alcohol, amine, carboxylic acid, ester, amide, ether, and acyl groups. $R^1$ to $R^8$ each desirably independently denote hydrogen, a methyl group, or a substituted or unsubstituted phenyl group, with hydrogen being preferred.

Compounds 8 to 11 in the embodiments described further below are examples of the compound denoted by general formula (1b), and are not to be construed as limitations. The compound of general formula (1b) can be obtained employing a starting material in the form of optically active (R,R)-1,1'-binaphthol (1). Optically active (S,S)-1,1'-binaphthol may be employed as starting material instead of optically active (R,R)-1,1'-binaphthol (1), and the compound of general formula (1a) may be obtained by the same method as for the compound denoted by general formula (1b).

The compound denoted by general formula (1a) or (1b) can be synthesized based on the following reaction scheme, for example, employing substituted or unsubstituted optically active 1,1'-binaphthol as starting material. Unsubstituted optically active 1,1'-binaphthol is commercially available. Depending on the substituent, substituted optically active 1,1'-binaphthols are also available. Even when such products are not commercially available, biphenols can be modified by brominating the 3,3' position or 6,6' position and then introducing a substituent in a cross-coupling reaction, for example (references: (1) Kobayashi, S.; Kusakabe, K-I.; Komiyama, S.; Ishitani, H. *J. Org. Chem.* 1999, 64, 4220-4221; (2) Qian, C.; Huang, T.; Zhu, C.; Sun, J. *J. Chem. Soc., Perkin Trans. 1* 1998, 2097).

[Chem. 17]
Syntheses of (R,R)-Linked-Phosphoramidite

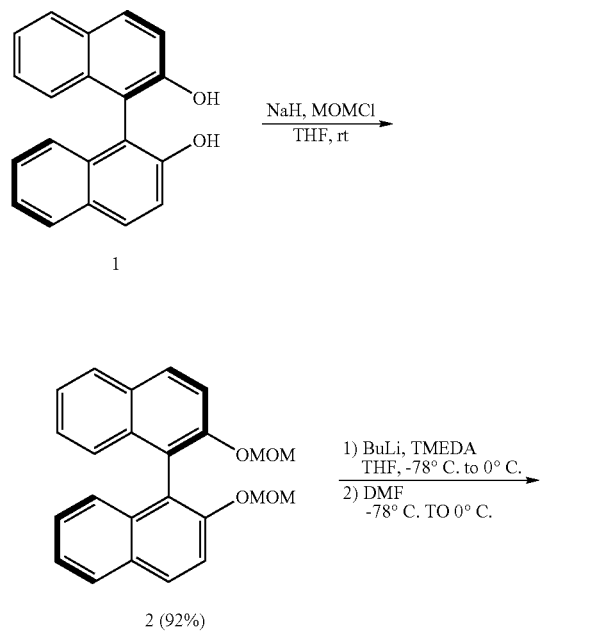

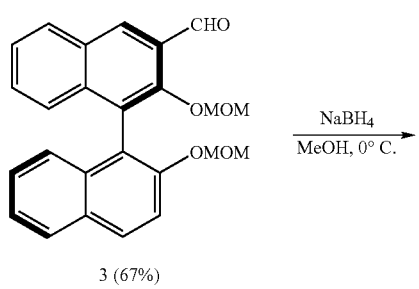

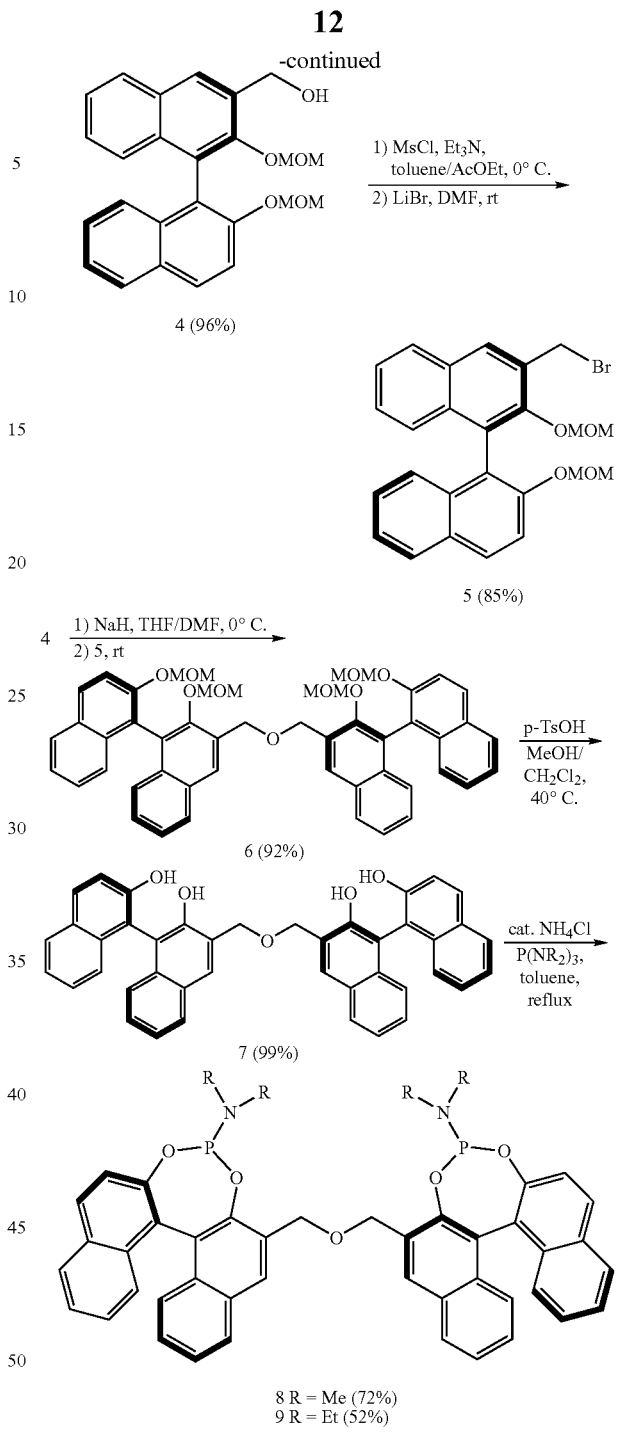

The above scheme is a synthesis example for a compound in which, in general formulas (a) and (b), X denotes oxygen, Y denotes $NR^{10}R^{11}$, n denotes 1, and $R^1$ to $R^8$ denote hydrogen. As indicated in the above scheme, the synthesis of compounds 1 to 7 can be conducted based on the methods described in the following references:

(1) Bougauchi, M.; Watanabe, S.; Arai, T.; Sasai, H.; Shibasaki, M. *J. Am. Chem. Soc.* 1997, 119, 2329-2330;
(2) Matsunaga, S.; Das, J.; Roels, J.; Vogl, E. M.; Yamamoto, N.; Iida, T.; Yamaguchi, K.; Shibasaki, M. *J. Am. Chem. Soc.* 2000, 122, 2252-2260;
(3) Japanese Unexamined Patent Publication (KOKAI) No. 2002-69076.

Synthesis from compound 7 to compounds 8, 9, and 11 (Y=NR$^{10}$R$^{11}$: phosphoramidite ligand) can be implemented based on the methods described in the following reference documents:
(1) Hulst, R.; Vries, N. K.; Feringa, B. L. *Tetrahedron Asymmetry*, 1994, 5, 699-708;
(2) Arnold, L. A.; Imbos, R.; Mandoli, A.; de Vries, A. H. M.; Naasz, R.; Feringa, B. L. *Tetrahedron* 2000, 56, 2865-2878.

A compound of general formula (1a) or (1b) in which Y denotes the phosphite ligand OR$^{12}$ (such as Compound 11) can be synthesized as follows. For example, for Compounds 7 to 11, toluene, phosphorus trichloride, and triethylamine are introduced, a toluene solution of Compound 7 is added dropwise at −60° C., and stirring is conducted for two hours. The reaction solution is heated to room temperature and filtered, after which triethylamine and alcohol are added at −40° C. The mixture is then stirred for 16 hours at room temperature. After distilling off the solvent, the residue is purified by silica gel chromatography, yielding Compound 11.

This synthesis method was developed by referring to the method of synthesizing Compound 10 (N(i-Pr)$_2$). Synthesis can also be conducted according to the general synthesis methods described in the following reference documents:
(1) WO0194278;
(2) Heteroatom Chemistry, 2002, 13, 93-95;
(3) EP1394168;
(4) Japanese Unexamined Patent Publication (KOKAI) No. 2000-53688.

A compound of general formula (1a) or (1b) in which Y denotes SR$^{13}$ can be synthesized from Compound 7 based on the methods described in the following reference documents:
(1) WO0194278;
(2) Japanese Unexamined Patent Publication (KOKAI) Showa No. 60-180794;
(3) *Z. Anorg. Allg. Chem.* 2000, 626, 1246.

The above scheme shows a method for synthesizing a compound in which X denotes oxygen in general formula (1a) or (1b). However, when X denotes carbon, sulfur, or nitrogen, the synthesis can be conducted as follows.

When X denotes carbon, for example, synthesis can be conducted from Compound 2 based on the method described in the following reference document:
Reference Document:
Matsunaga, S.; Das, J.; Roels, J.; Vogel, E. M.; Yamamoto, N.; Iida, T.; Yamaguchi, K.; Shibasaki, M. J. Am. Chem. Soc. 2000, 122, 2252-2260.

When X denotes nitrogen, a compound crosslinked with nitrogen can be synthesized by reacting Compound 5 with a primary amine in the presence of a base.
Reference Document:
Majima, K.; Takita, R.; Okada, A.; Ohshima, T.; Shibasaki, M. *J. Am. Chem. Soc.* 2003, 125, 15837-15845.

When X denotes sulfur, a sulfur-crosslinked compound can be synthesized by thioetherizing Compound 5 and a thiol obtained by hydrolysis of 3-thioacetoxymethyl-2,2'-bis(methoxymethyloxy)-1,1'-binaphthalene obtained by reacting Compound 5 with potassium thioacetate.
Reference Document:
Kumagai, N.; Matsunaga, S.; Kinoshita, T.; Harada, S.; Okada, S.; Sakamoto, S.; Yamaguchi, K.; Shibasaki, M. *J. Am. Chem. Soc.* 2003, 125, 2169-2178.

Further, the above scheme shows a method of synthesizing a compound in which n denotes 1 in general formula (1); compounds in which n denotes 2 or 3 can be synthesized as follows.

When n denotes 2, reaction of ethylene oxide with an anion obtained by stripping off the hydrogen at position 3 with a base such as n-BuLi, and when n denotes 3, reaction of trimethylene oxide with the same yields an alcohol having a corresponding methylene chain. Synthesis is possible by etherization following similar bromination as same as that of Compound 4.
Reference Documents:
Matsunaga, S.; Das, J.; Roels, J.; Vogel, E. M.; Yamamoto, N.; Iida, T.; Yamaguchi, K.; Shibasaki, M. *J. Am. Chem. Soc.* 2000, 122, 2252-2260.
Yoshikawa, N.; Shibasaki, M. *Tetrahedron* 2001, 57, 2569-2579.

[The Catalyst]

The present invention relates to a complex (rhodium complex catalyst, iridium complex catalyst, and ruthenium complex catalyst), the core metal of which is rhodium, iridium, or ruthenium, comprising the compound denoted by general formula (1a) or (1b) as ligand. The complex catalyst of the present invention is denoted by general formula (20) below.

$$M^1X_mL^1_pL^2_q \quad (20)$$

In the formula, M$^1$ denotes rhodium, iridium, or ruthenium; X denotes a halogen; RO (where RO denotes one or more member of the group consisting of hydroxy, alkoxy, acetyl acetonate, acetoxy, and trifluoromethane sulfonate), a BF$_4$, ClO$_4$, PF$_6$, B(Ar)$_4$, or SbF$_6$ anion, or hydrogen; m denotes an integer of from 1 to 3; L$^1$ denotes an olefin, eta$^3$-allyl, aryl (Ar) group, amine, carbon monoxide, or acetonitrile; p denotes an integer of from 0 to 3; L$^2$ denotes the compound represented by general formula (1a) or (1b) in [1]; q denotes the integer 1 or 2; and aryl (Ar) denotes an aromatic ring).

A rhodium complex catalyst is desirable as the above complex catalyst. This rhodium complex catalyst is desirably denoted by general equation (20a) below:

$$RhX_mL^1_pL^2_q \quad (20a)$$

In the formula, X denotes a halogen, RO (wherein RO denotes a member selected from the group consisting of hydroxy, alkoxy, acetyl acetonate, acetoxy, and trifluoromethane sulfonate), or a BF$_4$, ClO$_4$, PF$_6$, B(Ar)$_4$, or SbF$_6$ anion. X desirably denotes a BF$_4$, ClO$_4$, PF$_6$, or SBF$_6$ anion; preferably a BF$_4$ anion.

m denotes an integer of from 1 to 3; desirably 1.

L$^1$ denotes an olefin such as ethylene, cyclooctene, norbornadiene, or cyclooctadiene; carbon monoxide; or acetonitrile. L$^1$ desirably denotes an olefin such as ethylene, cyclooctene, norbornadiene, or cyclooctadiene; preferably norbornadiene.

p denotes an integer of from 0 to 3; preferably 1.

L$^2$ denotes the compound represented by general formula (1a) or (1b).

q denotes the integer 1 or 2; preferably 1.

The rhodium complex catalyst of the present invention with a rhodium core metal can be prepared by mixing a rhodium complex such as [Rh(nbd)$_2$]BF$_4$ or [RhCl(coe)$_2$]$_2$ and a ligand in the form of the compound denoted by general formula (1a) or (1b) in a suitable solvent such as dioxane, 1,2-dimethoxyethane, methylene chloride, or water. The rhodium complex catalyst of the present invention thus prepared can be employed as is, or the solvent can be distilled off and the residue recrystallized to obtain a complex catalyst.

The iridium complex catalyst of the present invention with an iridium core metal can be prepared by mixing an iridium complex such as [IrCl(cyclooctadiene)]$_2$ or IrH(CO)(PPh$_3$)$_3$ and a ligand in the form of the compound denoted by general formula (1a) or (1b) in a suitable solvent such as dioxane, 1,2-dimethoxyethane, methylene chloride, or water in the same manner as for the above-described rhodium complex catalyst of the present invention. The iridium complex catalyst of the present invention thus prepared can be employed as is, or the solvent can be distilled off and the residue recrystallized to obtain a complex catalyst.

The ruthenium complex catalyst of the present invention with a ruthenium core can be prepared by mixing a ruthenium complex such as $[RuCl_2(C_6H_6)]_2$ or $[RuCl_2(\text{p-cymene})]_2$ and a ligand in the form of the compound denoted by general formula (1a) or (1b) in a suitable solvent such as dioxane, 1,2-dimethoxyethane, methylene chloride, or water in the same manner as for the above-described rhodium complex catalyst of the present invention. The ruthenium complex catalyst of the present invention thus prepared can be employed as is, or the solvent can be distilled off and the residue recrystallized to obtain a complex catalyst.

The rhodium complex catalyst, iridium complex catalyst, and ruthenium complex catalyst of the present invention denoted by general formula (20) can be employed as catalysts for the synthesis of optically active beta-substituted carbonyl compounds. Alternatively, the rhodium complex catalyst, iridium complex catalyst, and ruthenium complex catalyst of the present invention denoted by general formula (20) can be employed as catalysts in asymmetric 1,2-addition reactions. Optically active beta-substituted carbonyl compound synthesis reactions and asymmetric 1,2-addition reactions will be described further below.

The present invention relates to complexes (palladium complex catalysts and platinum complex catalysts) comprising a core metal in the form of palladium or platinum and a ligand in the form of the compound denoted by general formula (1a) or (1b) above. The palladium complex catalyst and platinum complex catalyst of the present invention can be denoted by general formula (21) below.

$$M^2X_rL^3_sL^4_t \quad (21)$$

(In the formula, $M^2$ denotes palladium or platinum; X denotes a halogen, acetate anion, or $BF_4$, $PF_6$, $ClO_4$, or $SbF_6$ anion; r denotes an integer of from 0 to 2; $L^3$ denotes a triaryl (or alkyl) phosphine, acetonitrile, benzonitrile, dibenzylidene acetone, or $eta^3$-allyl; s denotes an integer of from 0 to 2; $L^4$ denotes the compound denoted by general formula (1a) or (1b) in [1] above; t denotes 1; and Ar denotes an aromatic ring.)

The above complex catalyst is desirably a palladium complex catalyst; the palladium complex catalyst is desirably denoted by general formula (21a) below:

$$PdX_rL^3_sL^4_t \quad (21a)$$

In the formula, X denotes a halogen, acetate anion, or $BF_4$, $PF_6$, $ClO_4$, $B(Ar)_4$, or $SbF_6$ anion. X desirably denotes a halogen, preferably chlorine.

r denotes an integer of from 0 to 2; preferably 0 or 1.

$L^3$ denotes a triaryl (or alkyl) phosphine, acetonitrile, benzonitrile, dibenzylidene acetone, or $eta^3$-allyl; preferably benzylidene acetone or an $eta^3$-allyl.

s denotes an integer of from 0 to 2; preferably 0.

$L^4$ denotes the compound denoted by general formula (1a) or (1b).

t denotes 1.

The palladium complex catalyst of the present invention can be prepared by mixing a palladium complex such as $[Pd(eta^3-C_3H_5)Cl]_2$ or $Pd_2 dba_3\text{-}CHCl_3$ and a ligand in the form of the compound denoted by general formula (1a) or (1b) in a suitable solvent such as dioxane, 1,2-dimethoxyethane, methylene chloride, or water. The palladium complex catalyst of the present invention thus prepared can be employed as is, or the solvent can be distilled off and the residue recrystallized to obtain a complex catalyst.

The platinum complex catalyst of the present invention can be prepared by mixing a platinum complex such as $PtCl_2$ (cyclooctadiene), $PtCl_2(CH_3CN)_2$, or $PtCl_2(PhCN)_2$ with a ligand in the form of the compound denoted by general formula (1a) or (1b) in a suitable solvent such as dioxane, 1,2-dimethoxyethane, methylene chloride, or water. The platinum complex catalyst of the present invention thus prepared can be employed as is, or the solvent can be distilled off and the residue recrystallized to obtain a complex catalyst.

The palladium complex catalyst and platinum complex catalyst of the present invention denoted by general formula (21) can be employed as catalysts in asymmetric allylic substitution reactions. Examples of asymmetric allylic substitution reactions are asymmetric allylic alkylation reactions and asymmetric allylic amination reactions. These asymmetric allylic substitution reactions will be described further below.

[Method for Manufacturing Optically Active Beta-Substituted Carbonyl Compounds]

The present invention relates to a method for manufacturing optically active beta-substituted carbonyl compounds by reacting a substituted or unsubstituted alpha, beta-unsaturated compound and an organic metal reagent, characterized by conducting the reaction in the presence of the rhodium complex catalyst, iridium complex catalyst, or ruthenium complex catalyst denoted by general formula (20).

The optically active beta-substituted carbonyl compound that is the target product of the above manufacturing method of the present invention can be denoted by general formula (4) below:

[Chem. 18]

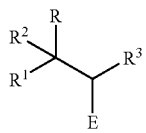

(4)

(wherein $R^1$, $R^2$, and $R^3$, which may be identical or different, each denote a hydrogen atom, alkyl group having 1 to 8 carbon atoms, alkoxy group having 1 to 8 carbon atoms, alkylthio group having 1 to 8 carbon atoms, or amino group optionally having an alkyl group with 1 to 8 carbon atoms; E denotes a carboxyl group, cyano group, carbamoyl group optionally having an alkyl group with 1 to 8 carbon atoms, or nitro group; and R denotes a substituted or unsubstituted alkyl, alkenyl, alkynyl, or aryl group, where R desirably denotes a substituted or unsubstituted aryl group).

Examples of substituents in the above alpha, beta-unsaturated compound are: carboxyl groups, alkoxycarbonyl groups, cyano groups, substituted carbamoyl groups, acyl groups, formyl groups, and nitro groups.

The above alpha, beta-unsaturated compound can be denoted by general formula (2) below:

[Chem. 19]

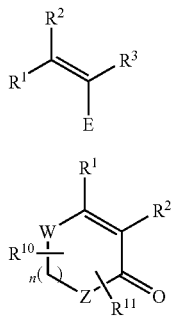

(2a)

(2b)

(wherein $R^1$, $R^2$, and $R^3$, which may be identical or different, each denote a hydrogen, alkyl group having 1 to 8 carbon atoms, alkoxy group having 1 to 8 carbon atoms, alkylthio group having 1 to 8 carbon atoms, or amino group optionally having an alkyl group with 1 to 8 carbon atoms; E denotes a carboxyl group, cyano group, carbamoyl group optionally having an alkyl group with 1 to 8 carbon atoms, or nitro group; n denotes an integer of 0 or above; W and Z, which may be identical or different, each denote —$CH_2$—, =CH—, —O—, —S—, —NH—, or =N—; $R^{10}$ and $R^{11}$, which may be identical or different, each denote a hydrogen atom, alkyl group having 1 to 8 carbon atoms, alkoxy group having 1 to 8 carbon atoms, nitro group, cyano group, acyl group having 2 to 8 carbon atoms, alkoxycarbonyl group having 2 to 8 carbon atoms, or amino group optionally having an alkyl group with 1 to 8 carbon atoms, or adjacent $R^{10}$ and $R^{11}$ denote general formula (a) below:

[Chem. 20]

(a)

(wherein $R^{12}$ denotes a hydrogen atom, alkyl group having 1 to 8 carbon atoms, alkoxy group having 1 to 8 carbon atoms, cyano group, halogenated alkyl group, halogen atom, carbamoyl group optionally having an alkyl group with 1 to 8 carbon atoms, acyl group having 2 to 8 carbon atoms, alkoxycarbonyl group having 2 to 8 carbon atoms, or amino group optionally having an alkyl group with 1 to 8 carbon atoms)).

The above organometallic reagent is a substituted or unsubstituted alkyl, alkenyl, alkynyl, or aryl compound of a metal. Examples of the metal are Mg, Zn, Cu, B, Al, Ga, In, Si, Ge, Sn, Pb, and Bi. The organometallic reagent is desirably an organic boronic acid derivative. The organic boronic acid derivative can be a compound denoted by general formula (3a), (3b), or (3c) below:

[Chem. 21]

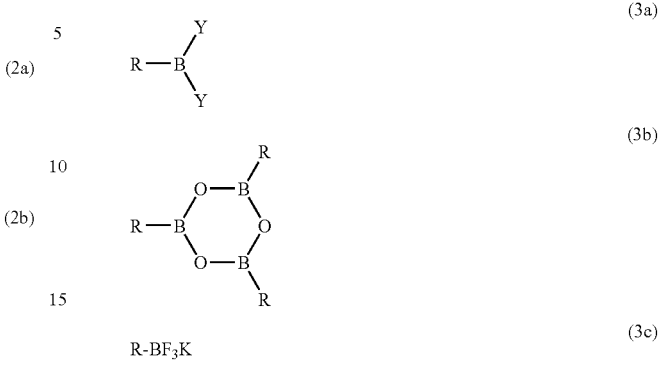

R-$BF_3$K (3c)

(wherein Y denotes a hydroxyl group, alkoxy group having 1 to 8 carbon atoms, phenoxy group optionally having an alkyl group with 1 to 8 carbon atoms, cyclohexyloxy group, or group denoted by formula a, b, c, or d below (in each of which q denotes an integer of from 1 to 4; r and s each independently denote an integer of from 0 to 5, and Me denotes a methyl group); and R denotes a substituted or unsubstituted alkyl, alkenyl, alkynyl, or aryl group, with R desirably denoting a substituted or unsubstituted aryl group).

[Chem. 22]

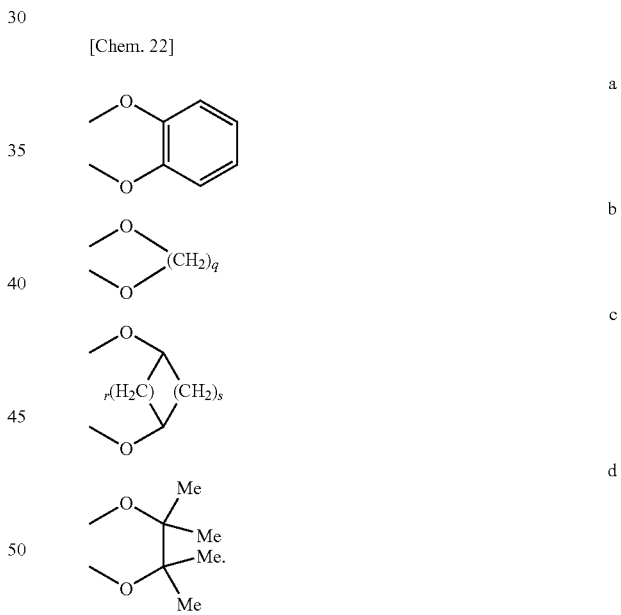

[Method for Manufacturing Optically Active Alcohol Compounds]

The present invention relates to a method for manufacturing optically active alcohol compounds by reacting an aldehyde compound and an organometallic reagent, characterized by conducting the reaction in the presence of the rhodium complex catalyst, iridium complex catalyst, or ruthenium complex catalyst denoted by general formula (20).

The optically active benzyl alcohol compound that is the target product of the above manufacturing method of the present invention can be denoted by general formula (7) below:

[Chem. 23]

(7)

In the formula, $R^4$ denotes a substituted or unsubstituted alkyl group or aryl group, with examples of the substituent being halogens, amino groups, carboxyl groups, alkoxycarbonyl groups, cyano groups, and carbamoyl groups (optionally substituted). Ar denotes an aromatic ring.

The above aldehyde compound may be a compound denoted by general formula (5):

$R^4CHO$ (5)

In the formula, $R^4$ denotes a substituted or unsubstituted alkyl group or aryl group, with examples of the substituent being halogens, amino groups, carboxyl groups, alkoxycarbonyl groups, cyano groups, and carbamoyl groups (optionally substituted).

The above organometallic reagent is a substituted or unsubstituted alkyl, alkenyl, alkynyl, or aryl compound of a metal. Examples of the metal are Mg, Zn, Cu, B, Al, Ga, In, Si, Ge, Sn, Pb, and Bi. The organometallic reagent is desirably an organic boronic acid derivative. The organoboronic acid derivative can be a compound denoted by general formula (3a), (3b), or (3c) below:

[Chem. 24]

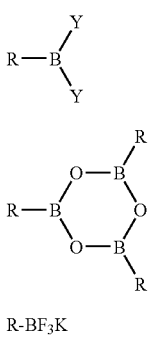

(3a)

(3b)

(3c)

(wherein Y denotes a hydroxyl group, alkoxy group having 1 to 8 carbon atoms, phenoxy group optionally having an alkyl group with 1 to 8 carbon atoms, cyclohexyloxy group, or group denoted by formula a, b, c, or d below (in each of which q denotes an integer of from 1 to 4; r and s each independently denote an integer of from 0 to 5, and Me denotes a methyl group); and R denotes a substituted or unsubstituted alkyl, alkenyl, alkynyl, or aryl group, with R desirably denoting a substituted or unsubstituted aryl group).

[Chem. 25]

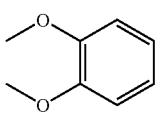

a

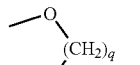
b

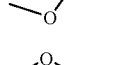
c

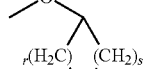

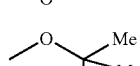
d

[Method for Manufacturing Optically Active (1,3-Disubstituted Propenyl)Dialkyl Malonate Compounds]

The present invention relates to a method for manufacturing optically active (1,3-disubstituted propenyl)dialkyl malonate compounds by reacting a 1,3-disubstituted allyl acetate compound and a dialkyl malonate compound, characterized by conducting the reaction in the presence of the palladium complex catalyst or platinum complex catalyst denoted by general formula (21).

The optically active (1,3-disubstituted propenyl)dialkyl malonate compound that is the target product of the above manufacturing method of the present invention can be denoted by general formula (10) below:

[Chem. 26]

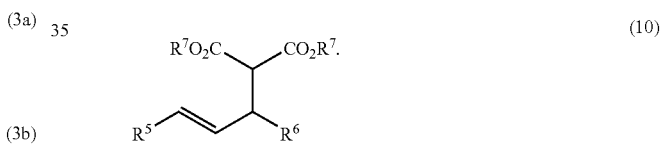
(10)

In the formula, $R^5$ and $R^6$ denote identical substituted or unsubstituted alkyl groups, or substituted or unsubstituted aryl groups.

The above 1,3-disubstituted allyl acetate compound can be denoted by general formula (8) below:

[Chem. 27]

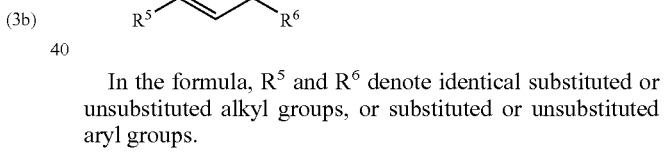
(8)

In the formula, $R^5$ and $R^6$ denote identical substituted or unsubstituted alkyl groups, or substituted or unsubstituted aryl groups.

The above dialkyl malonate can be denoted by general formula (9) below:

[Chem. 28]

(9)

$R^7$ denotes a substituted or unsubstituted alkyl group.

[Method for Manufacturing Optically Active Allylamine Compounds]

The present invention relates to a method for manufacturing optically active allylamine compounds by reacting a 1,3-disubstituted allyl acetate compound with an amine compound, characterized by conducting the reaction in the presence of the palladium complex catalyst or platinum complex catalyst denoted by general formula (21).

The optically active allylamine compound that is the target product of the above manufacturing method of the present invention can be denoted by general formula (13) below:

[Chem. 29]

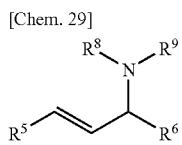

(13)

$R^5$ and $R^6$ denote identical substituted or unsubstituted alkyl groups or substituted or unsubstituted aryl groups; and $R^8$ and $R^9$ each independently denote hydrogen, a substituted or unsubstituted alkyl group, or a substituted or unsubstituted aryl group, it being permissible for $R^8$ and $R^9$ to form a ring having 3 to 7 carbon atoms.

The above 1,3-disubstituted allylamine compound can be denoted by general formula (11) below:

[Chem. 30]

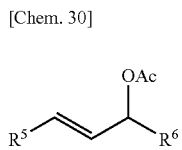

(11)

$R^5$ and $R^6$ denote identical substituted or unsubstituted alkyl groups or substituted or unsubstituted aryl groups.

The above amine compound can be denoted by general formula (12) below:

[Chem. 31]

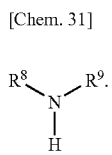

(12)

$R^8$ and $R^9$ each independently denote hydrogen, a substituted or unsubstituted alkyl group, or a substituted or unsubstituted aryl group, it being permissible for $R^8$ and $R^9$ to form a ring having 3 to 7 carbon atoms. Specifically, general formula (12) can denote a primary amine such as benzylamine or aniline, a secondary amine such as pyrrolidine, or potassium phthalimide.

In addition to being employed in the above reactions, the above described rhodium complex catalyst, iridium complex catalyst, ruthenium complex catalyst, and platinum complex catalyst of the present invention can be employed as catalysts for the asymmetric hydrogenation of alkenes, ketones, and the like. Here, the alkene may be a compound denoted by general formula (13):

[Chem. 32]

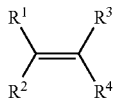

(13)

$R^1$, $R^2$, $R^3$, and $R^4$ each independently denote an alkyl group having 1 to 8 carbon atoms, aryl group, alkoxy group having 1 to 8 carbon atoms, nitro group, cyano group, acyl group having 2 to 8 carbon atoms, alkoxycarbonyl group having 2 to 8 carbon atoms, amino group optionally having an alkyl group with 1 to 8 carbon atoms, or carbamoyl group optionally having an alkyl group with 1 to 8 carbon atoms, where any one from among $R^1$, $R^2$, $R^3$, and $R^4$ may denote hydrogen.

Here, the ketone may be a compound denoted by general formula (14):

[Chem. 33]

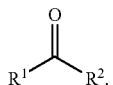

(14)

$R^1$ and $R^2$ each independently denote a substituted or unsubstituted alkyl, alkenyl, alkynyl, or aryl group.

In the present Description, unless specifically stated otherwise, the alkyl group is a linear or branched alkyl group having 1 to 8 carbon atoms, preferably a methyl group, ethyl group, or iso-propyl group, for example. Examples of the substituents in substituted alkyl and aryl groups are alcohol, amine, carboxylic acid, ester, amide, ether, and acyl groups.

EMBODIMENTS

The present invention is described in greater detail below through embodiments.

REFERENCE EXAMPLE 1

Synthesis of Compounds 1 to 7

The synthesis scheme employed for Compounds 1 to 7 was as set forth above.

Synthesis of Compound 2

NaH (60 percent dispersion in mineral oil) (250 mmol) was charged to a 500 mL round-bottomed flask. The flask was backfilled with argon and the mixture was washed 2 to 3 times with THF. THF (100 mL) was added and (R,R)-1,1'-binaphthol (50 mmol) dissolved in THF (125 mL) was added. The mixture was stirred for one hour at 0° C., after which a solution of chloromethyl ethyl ether (125 mL) in THF (30 mL) was added dropwise. The mixture was then stirred for three hours at room temperature. Methanol and water were added and the mixture was extracted three times with diethyl ether. The organic layer was washed with saturated sodium carbonate solution and saturated brine, and then dried with anhydrous sodium sulfate. The solvent was distilled off and the residue was recrystallized from methylene chloride/pentane (yield 92 percent).

Synthesis of Compound 3

A THF (120 mL) solution of (R,R)-2,2'-bis-methoxymethoxy-1,1'-binaphthol (Compound 2) (46 mmol)

was charged to a 200 mL flask and cooled to −78° C., N,N, N',N'-tetramethylethylenediamine (66 mmol) was added, after which n-butyllithium was added dropwise. The mixture was stirred for 30 minutes at 0° C., a THF solution of N,N-dimethylformamide was added dropwise at −78° C., and the mixture was stirred for 30 minutes. The temperature was increased to 0° C. and the mixture was stirred for 40 minutes. Saturated ammonium chloride aqueous solution and 1 N hydrochloric acid were added. The mixture was extracted with diethyl ether. The organic layer was dried with anhydrous sodium sulfate, the solvent was distilled off, and the residue was purified by silica gel chromatography. The product was then recrystallized from methylene chloride/hexane (yield 67 percent).

Synthesis of Compound 4

(R,R)-2,2'-bismethoxymethoxy-1,1'-binaphthol-3-carboxyaldehyde (Compound 3) (25 mmol) was charged to a 500 mL round-bottomed flask, THF (120 mL) and MeOH (120 mL) were added, sodium borohydride (27.5 mmol) was added at 0° C., and the mixture was stirred for 15 minutes. Water was added to stop the reaction, after which the solvent was distilled off under reduced pressure at room temperature. A saturated ammonium hydride aqueous solution was added, the mixture was extracted with ethyl acetate, and the organic layer was washed with saturated brine, and dried with anhydrous sodium sulfate. The solvent was distilled off and the residue was purified by silica gel chromatography (yield 96 percent).

Synthesis of Compound 5

An ethyl acetate solution of (R,R)-3-hydroxymethyl-2,2'-bismethoxymethoxy-1,1'-binapthalene (Compound 4) was charged to a 300 mL flask and toluene and ethyl acetate were added. Triethylamine was added at 0° C., followed by the addition of methanesulfonyl chloride. The mixture was stirred for 90 minutes and then filtered. A DMF solution of lithium bromide was added to the filtrate at 0° C., and the mixture was warm up to room temperature. Following extraction with diethyl ether, the organic layer was washed with 1 N hydrochloric acid, saturated sodium carbonate aqueous solution, and saturated brine, and then dried with anhydrous sodium sulfate. The solvent was distilled off, yielding Compound 5 (yield 85 percent).

Synthesis of Compound 6

A THF/DMF solution of (R,R)-3-hydroxymethyl-2,2'-bismethoxymethoxy-1,1'-binapthalene (Compound 4) was charged to a 200 mL flask, a THF/DMF solution of NaH that had been washed with THF was added dropwise at 0° C., and the mixture was stirred for one hour. A DMF solution of (R,R)-3-bromomethyl-2,2'-bismethoxymethoxy-1,1'-binaphthalene (Compound 5) was added dropwise, the mixture was warm up to room temperature, and the mixture was stirred for 64 hours. Water was added at 0° C. to stop the reaction, after which the reaction solution was extracted with diethyl ether, washed with saturated brine, and dried with anhydrous sodium sulfate. After distilling off the solvent, the residue was purified by silica gel chromatography (yield 92 percent).

Synthesis of Compound 7

Compound 6 was charged to a 200 mL flask, methylene chloride/methanol was added, and p-toluenesulfonic acid monohydrate was added. After being stirred for 36 hours at 40° C., the mixture was extracted with methylene chloride, washed with saturated sodium carbonate aqueous solution and saturated brine, and dried with anhydrous sodium sulfate. The solvent was distilled off and the residue was purified by silica gel chromatography (yield 99 percent).

Embodiment 1

Synthesis of Compounds 8 and 9

Ammonium chloride (0.01 g) and Compound 7 (1 mmol) were charged to a 30 mL flask. The mixture was dissolved in toluene (10 mL), hexamethyl phosphorus triamide was added, and the mixture was refluxed for 12 hours.

After allowing the mixture to cool to room temperature, the solvent was distilled off. The residue was recrystallized from methylene chloride/pentane (yield 75 percent, R=Me).

[Chem. 34]

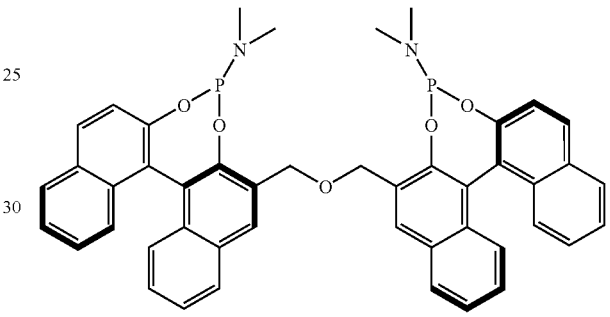

Structural formula and spectral data for R=Me (Compound 8)

Linked-phosphoramidaite from (R)-BINOL $C_{46}H_{38}N_2O_5P_2$ Mol. Wt.: 761

$^1$H-NMR (CD$_2$Cl$_2$) δ=2.23-2.39 (m, 12H), 4.82 (d, J=13.3 Hz, 2H), 5.02 (d, J=13.3 Hz, 2H), 7.07-7.39 (m, 14H), 7.76-7.86 (m, 6H), 8.15 (s, 2H) $^{31}$P-NMR (CD$_2$Cl$_2$) δ=150.8 ppm MS (FAB), m/z(%): 43(33), 266(28), 282(50), 329(100), 373(29), 388(24), 716(28), 761(M+H, 19)

HRMS (FAB) calcd for C46H39N2O5P2 761.2334, found 761.2334

[Chem. 35]

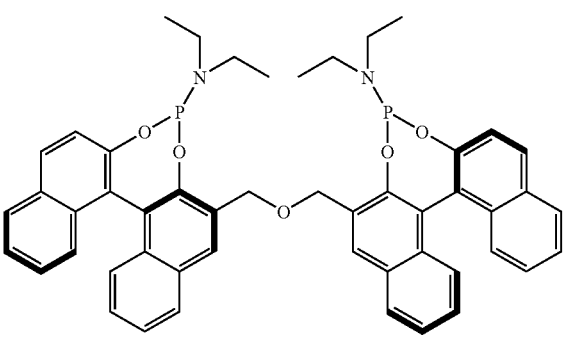

Structural Formula and Spectral Data for Compound 9

$^1$H-NMR (CD$_2$Cl$_2$) δ=0.75-0.91 (m, 12H), 2.64-2.95 (m, 8H), 4.89 (d, J=13.6 Hz, 2H), 5.06 (d, J=13.6 Hz, 2H), 7.09-7.41 (m, 14H), 7.79-7.87 (m, 6H), 8.15 (d, J=8.8 Hz, 2H)

$^{31}$P-NMR (CD$_2$Cl$_2$) δ=151.5 ppm

MS (FAB), m/z(%): 72(31), 266(38), 282(51), 329(100), 416(15), 744(28), 817(M+H, 10)

HRMS (FAB): calcd for C50H47N2O5P2 817.2960, found 817.2960

Embodiment 2

Method of Synthesizing Compound 10

Toluene (3 mL), PCl$_3$ (2 mmol), and NEt$_3$ (4 mmol) were charged to a flask, the mixture was cooled to −60° C., a toluene solution of Compound 7 was added dropwise, and the mixture was stirred for two hours. The mixture was warm up to room temperature and the salt that formed was filtered out. The filtrate was cooled to −40° C., n-BuLi (2 mmol) and diisopropylamine (3 mmol) were added, the mixture was warm up to room temperature, and the mixture was stirred for 16 hours. After distilling off the solvent, the residue was recrystallized from methylene chloride/pentane, yielding Compound 10.

Embodiment 3

Method of Synthesizing Compound 11

Toluene (3 mL), PCl$_3$ (2 mmol), and NEt$_3$ (4 mmol) were charged to a flask, the mixture was cooled to −60° C., a toluene solution of Compound 7 was added dropwise, and the mixture was stirred for two hours. The mixture was warm up to room temperature and the salt that formed was filtered out. The filtrate was again cooled to −40° C., phenol was added, and the mixture was stirred for 16 hours at room temperature. The solvent was distilled off and the residue was purified by silica gel chromatography, yielding Compound 11.

[Chem. 36]

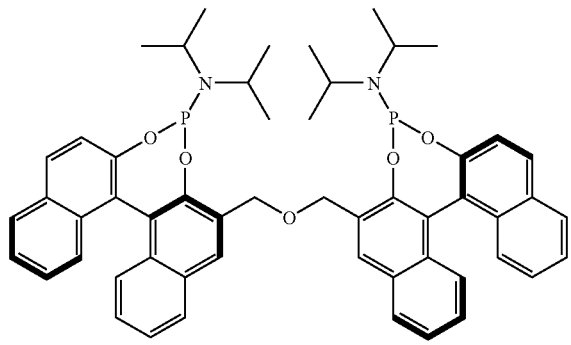

Structural Formula and Spectral Data for Compound 10

$^1$H-NMR (CD$_2$Cl$_2$) δ=0.78-1.36 (m, 24H), 3.24-3.32 (m, 4H), 5.03 (s, 4H), 7.12-7.39 (m, 14H), 7.92-7.97 (m, 6H), 8.23 (s, 2H)

$^{31}$P-NMR (CD$_2$Cl$_2$) δ=152.1 ppm

MS (FAB), m/z(%): 43(31), 57(32), 149(100), 266(25), 281(50), 329(87), 391(28), 429(50), 444(50), 772(18), 873 (M+H, 43)

HRMS (FAB) calcd for C54H55N2O5P2 873.3604, found 873.3604

[Chem. 37]

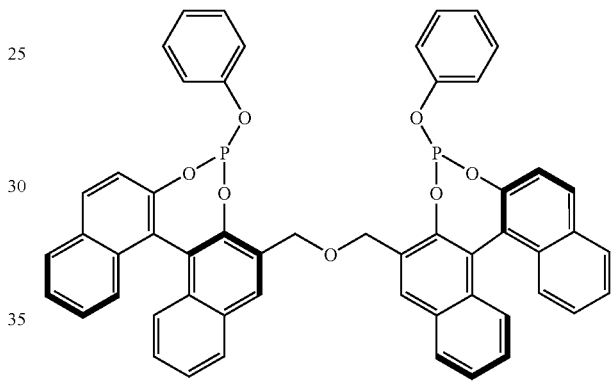

Structural Formula and Spectral Data for Compound 11

$^1$H-NMR (CD$_2$Cl$_2$) δ=4.77-4.86 (m, 2H), 4.98-5.12 (m, 2H), 7.24-7.43 (m, 24H), 7.84-7.92 (m, 6H), 8.18 (s, 2H)

$^{31}$P-NMR (CD$_2$Cl$_2$) δ=146.8

MS (FAB), m/z(%): 55(18), 77(20), 89(19), 107(20), 136 (78), 154(100), 281(31), 307(18), 329(10), 421(26), 469(12), 765(13), 824(11), 859(16)

HRMS (FAB) calcd for C54H37O7P2 859.2004, found 859.2004

Embodiment 4

Preparation of Rhodium Complex Catalyst

Under an argon atmosphere, rhodium catalyst (0.03 mmol) and ligand (Compound 8) (0.033 mmol) were added, dioxane (or 1,2-dimethoxyethane)/water (2.6 mL/0.4 mL) was added, and the mixture was stirred for one hour to prepare rhodium complex catalyst. The solution of rhodium complex catalyst obtained can normally be employed in reactions.

A complex was prepared by mixing rhodium complex and ligand (Compound 8) in methylene chloride. The solvent was distilled off and the residue was recrystallized to obtain a complex catalyst. The spectral data obtained for the rhodium complex catalyst when rhodium catalysts in the form of [Rh (nbd)$_2$]BF$_4$ and [RhCl(coe)$_2$]$_2$ were employed are given below.

[Chem. 38]

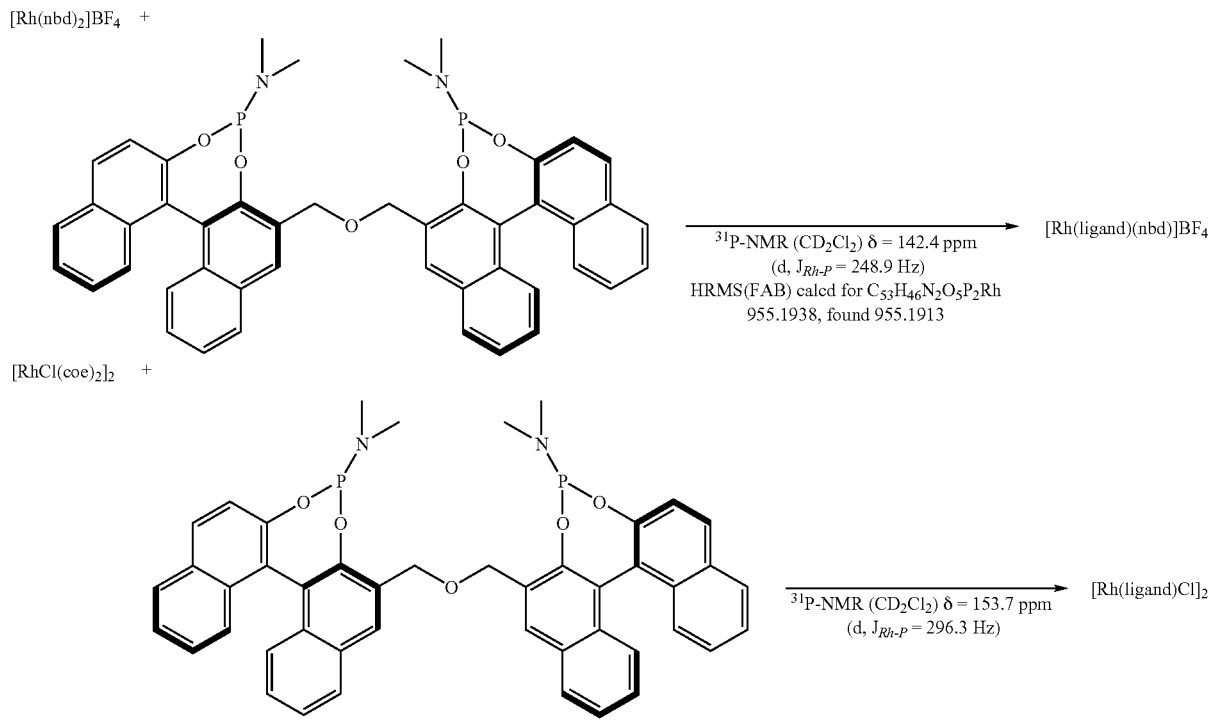

Embodiment 5

Synthesis of Optically Active Beta-Aryl Compounds

Under an argon atmosphere, rhodium catalyst (0.03 mmol) and ligand (0.033 mmol) were added, dioxane/water (2.6 mL/0.4 mL) was added, the mixture was stirred for one hour at room temperature, an alpha, beta-unsaturated carbonyl compound (1 mmol) and boronic acid (1.5 mmol) were added, and the mixture was stirred for several hours at room temperature. Following extraction, the mixture was dried with anhydrous sodium sulfate and purified by silica gel chromatography. The optical purity was determined by high-performance liquid chromatography using an optically active column.

Examination of reaction conditions: Optimal conditions for various rhodium catalysts and bases were explored, revealing that the optimal conditions were [Rh(nbd)$_2$]BF$_4$, Compound 8, and triethyl amine (Test 13).

TABLE 1

1,4-Addition of phenylboronic acid[a] to 2-cyclohexenone

| Run | Rh complex | Ligand | Base | Yield/ %[b] | % ee[c] |
|---|---|---|---|---|---|
| 1 | [RhCl(coe)$_2$]$_2$ | Compound 8 | none | trace | — |
| 2 | [RhCl(coe)$_2$]$_2$ | Compound 8 | K$_2$CO$_3$ | 26 | 98 |
| 3 | [RhCl(coe)$_2$]$_2$ | Compound 8 | K$_2$HPO$_4$ | 63 | 82 |
| 4 | [RhCl(coe)$_2$]$_2$ | Compound 8 | K$_3$PO$_4$ | 90 | 94 |
| 5 | [RhCl(coe)$_2$]$_2$ | Compound 8 | KOH | 84 | 98 |
| 6 | [RhCl(coe)$_2$]$_2$ | Compound 8 | NEt$_3$ | 46 | 97 |
| 7 | [RhCl(cod)$_2$]$_2$ | Compound 8 | KOH | 87 | 41 |
| 8 | Rh(acac)(C$_2$H$_4$)$_2$ | Compound 8 | KOH | 84 | 90 |
| 9 | [Rh(nbd)$_2$]BF$_4$ | Compound 8 | KOH | 80 | 89 |
| 10 | [Rh(nbd)$_2$]BF$_4$ | Compound 8 | K$_2$HPO$_4$ | 90 | 99 |

TABLE 1-continued 1,4-Addition of phenylboronic acid[a] to 2-cyclohexenone

| Run | Rh complex | Ligand | Base | Yield/ %[b] | % ee[c] |
|---|---|---|---|---|---|
| 11 | [Rh(nbd)$_2$]BF$_4$ | Compound 8 | K$_3$PO$_4$ | 92 | 99 |
| 12 | [Rh(nbd)$_2$]BF$_4$ | Compound 8 | NEt$_3$ | 94 | 99 |
| 13 | [Rh(nbd)$_2$]BF$_4$ | Compound 8 | NEt$_3$ | 99 | 99.6[d] |
| 14 | [Rh(nbd)$_2$]BF$_4$ | Compound 9 | NEt$_3$ | 62 | 83[e] |
| 15 | [Rh(nbd)$_2$]BF$_4$ | Compound 10 | NEt$_3$ | trace | —[e] |

[a]All the reactions were conducted in the presence of 2-cyclohexenone (1 mmol), phenylboronic acid (1.5 mmol), rhodium (I) complex (3 mol %, based on Rh), ligand (3.3 mol %), and a base (1 mmol when used) in dioxane (2.6 mL) and H$_2$O (0.43 mL) at 50° C. for 16 hours.
[b]The GC yield, based on 2-cyclohexenone.
[c]HPLC analysis using Dicel Chiralcel AD (hexane/2-propanol = 98/2)
[d]0.5 hour at 25° C.
[e]Two hours at 25° C.

[Chem. 39]

Compound 8

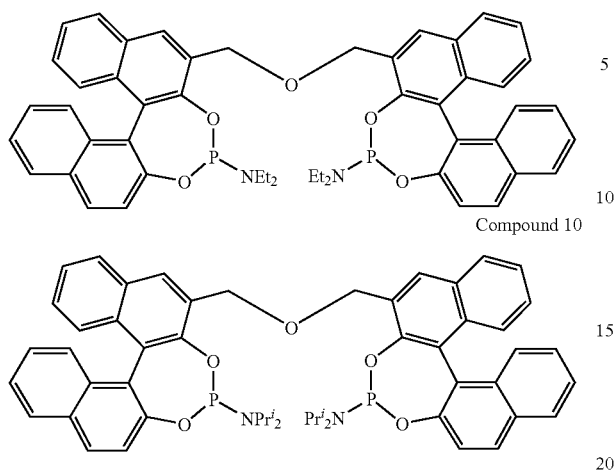

Compound 9

Compound 10

TABLE 2

1,4-Addition of arylboronic acid to alpha, beta-unsaturated carbonyl compounds

|   | Carbonyl compound employed | ArB(OH)$_2$ (X=) | [RhCl(coe)$_2$]$_2$/KOH[a] yield/%[c] | % ee[d] | [Rh(nbd)$_2$]BF$_4$/NEt$_3$[b] yield/%[c] | % ee[d] |
|---|---|---|---|---|---|---|
| 1 | 2-cyclopentenone | 3-Cl | 53 | 87 | 99 | 96 |
| 2 |  | 4-MeO | — | — | 99 | 96 |
| 3 | 2-cyclohexenone | H | 84 | 98 | 99 | 99.6[e] |
| 4 |  | 3-MeO | 77 | 99 | 90 | 99.5 |
| 5 |  | 4-MeO | 88 | 98 | 99 | 99.8 |
| 6 |  | 3-Cl | 95 | 98 | 86 | 99.8 |
| 7 | 2-cycloheptenone | H | 48 | 90 | 90 | 98 |
| 8 | (E)-C$_5$H$_{11}$CH=CHCOCH$_3$ | H | 84 | 67 | 87 (42[f]) | 74 (84[f]) |
| 9 |  | H | — | — | 99 | 5[g] |
| 10 |  | H | — | — | trace | —[h] |
| 11 |  | 3-MeO | 99 | 67 | 98 (65[f]) | 80 (83[f]) |
| 12 |  | 3-MeO (80° C.) | 98 | 71 | — | — |
| 13 |  | 3-F | 89 | 75 | 97 | 81 |
| 14 | (E)-i-C$_3$H$_7$CH=CHCOCH$_3$ | H | 72 | 88 | 80 | 92[i] |
| 15 |  | 3-MeO | 80 | 86 | 78 | 94[j] |
| 16 |  | 3-F | 66 | 81 | 71 | 90[j] |
| 17 | (E)-cyclo-C$_6$H$_{11}$CH=CHCOCH$_3$ | 3-MeO | — | — | 81 | 86[k] |
| 18 | (E)-i-C$_3$H$_7$CH=CHCO-cyclo-C$_6$H$_{11}$ | 3-MeO | — | — | 62 | 81 |
| 19 | (E)-C$_5$H$_{11}$CH=CHCOC$_6$H$_5$ | 3-MeO | — | — | 91 | 85 |
| 20 | (E)-i-C$_3$H$_7$CH=CHCOC$_6$H$_5$ | 3-MeO | — | — | 98 | 85[i] |
| 21 | (E)-C$_6$H$_5$CH=CHCOCH$_3$ | 3-MeO | — | — | 99 | 78 |
| 22 | (E)-C$_6$H$_5$CH=CHCOC$_6$H$_5$ | 3-MeO | — | — | 98 | 66[i] |
| 23 | (E)-naphthyl-CH=CHCOCH$_3$ | 3-MeO | — | — | 93 | 89[i] |
| 24 | (Z)-C$_3$H$_7$CH=CHCOC$_2$H$_5$ | 3-MeO | — | — | 64 | 1 |
| 25 | (Z)-C$_3$H$_7$CH=CHCOCH(C$_2$H$_5$)C$_2$H$_5$ | 3-MeO | — | — | 69 | 10[i] |
| 26 | (E)-C$_6$H$_5$CH=CHCO$_2$Et | 3-MeO | — | — | 48 | 65[m] |
| 27 | (E)-CH$_3$CH=CHCO$_2$Me | 3-MeO | — | — | 57 | 75[m] |
| 28 | (E)-CH$_3$CH=CHCO$_2$Et | 3-MeO | 94 | 56 | — | — |
| 29 | (E)-CH$_3$CH=CHCO$_2$$^i$Pr | 3-MeO | 90 | 57 | 33 | 70[m] |
| 30 | (E)-CH$_3$CH=CHCHO | 3-MeO | 47 | 41 | 60 | 68[i] |
| 31 | (E)-C$_6$H$_5$CH=CHCHO | 3-MeO | — | — | 16 | 92[i] |
| 32 | 5H-furan-2-one | H | — | — | 68 | 77[i] |
| 33 | 5,6-dihydro-2H-pyran-2-one | H | — | — | 72 | 89[i] |

TABLE 2-continued 1,4-Addition of arylboronic acid to alpha, beta-unsaturated carbonyl compounds

| Carbonyl compound employed | ArB(OH)$_2$ (X=) | [RhCl(coe)$_2$]$_2$/KOH[a] yield/%[c] | % ee[d] | [Rh(nbd)$_2$]BF$_4$/NEt$_3$[b] yield/%[c] | % ee[d] |
|---|---|---|---|---|---|
| 34  5,6-dihydro-2H-pyran-2-one | 3-MeO | — | — | 61 | 91[n] |
| 35  (E)-CH$_3$CH=CHCONCH$_2$C$_6$H$_5$ | 3-MeO | 43 | 63[o] | — | — |

[a]The reaction was conducted in dioxane (2.6 mL) and H$_2$O (0.43 mL) in the presence of enone (1 mmol), arylboronic acid (1.5 mmol), [RhCl(coe)$_2$]$_2$ (3 mol %, based on Rh), Compound 8 (3.3 mol %), and KOH (1 mmol) for 16 hours at 50° C.
[b]The reaction was conducted in dioxane (2.6 mL) and H$_2$O (0.43 mL) in the presence of enone (1 mmol), arylboronic acid (1.5 mmol), [Rh(nbd)$_2$]BF$_4$ (3 mol %, based on Rh), Compound 8 (3.3 mol %), and NEt$_3$ (1 mmol) for 2 hours at 25° C.
[c]Isolation yield, based on enone
[d]HPLC analysis employed Dicel Chiralcel.
[e]0.5 h at 25° C.
[f]48 h at 5° C.
[g]Compound 9 employed.
[h]Compound 10 employed
[i]6 h at 25° C.
[j]16 h at 25° C.
[k]2.5 equivalent of arylboronic acid employed; 10 h at 25° C.
[l]3 h at 25° C.
[m]24 h at 25° C.
[n]12 h at 25° C.
[o]Using K$_2$HPO$_4$ as base.

Embodiment 6

[Asymmetric 1,2-Addition Reaction]

Under an argon atmosphere, rhodium catalyst (0.03 mmol), ligand (0.033 mmol), and 1,2-dimethoxyethane (3 mL) were added and the mixture was stirred for one hour at room temperature. Water (3 mL), aldehyde (1 mmol), and arylboronic acid (2 mmol) were then added and the mixture was stirred for 48 hours at 60° C. Following ether extraction, the product was purified by column chromatography. The optical purity was determined by high-performance liquid chromatography using an optically active column.

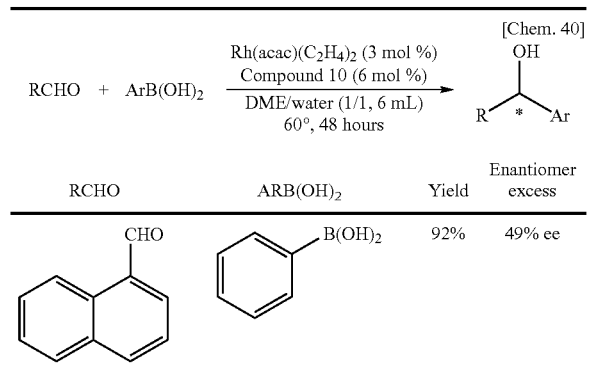

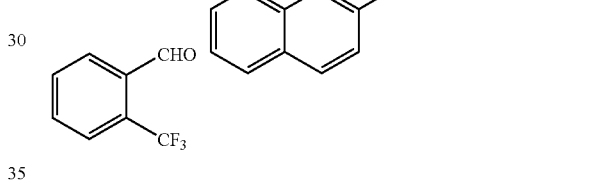

COMPARATIVE EXAMPLE 1

The same reaction was conducted by the method described in Nonpatent Reference Document 6 (Sakai, M.; Ueda, M.; Miyaura, N. *Angew. Chem. Int. Ed.* 1998, 37, 3279-3281). As a result, the yield and selectivity were both low, as indicated below. As shown in Embodiment 6 above, the use of ligand 10 of the present invention produced the target compound at high yield and improved the optical purity by about 10% ee.

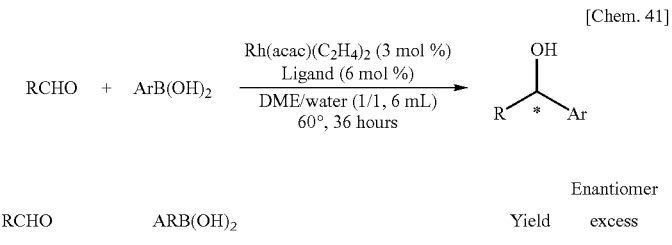

-continued

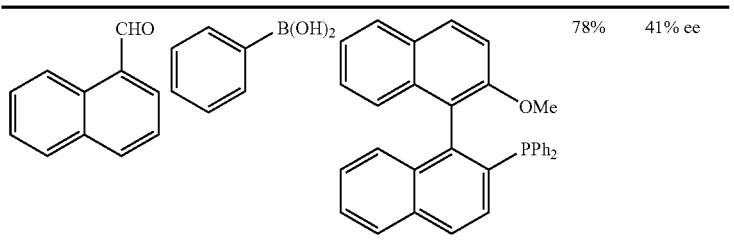

78%   41% ee

Embodiment 7

[Asymmetric Allylic Alkylation Reaction]

To a 20 mL flask were charged a palladium catalyst (0.03 mmol), ligand (0.033 mmol), and methylene chloride (3 mL) and the mixture was stirred for one hour. To this were added N,O-bis(trimethylsilyl)acetamide (1 mmol), dimethyl malonate (1 mmol), 1,3-diphenylpropenyl acetate, and potassium acetate and the mixture was stirred for 20 hours at room temperature. Following ether extraction, the product was purified by column chromatography. The optical purity was determined by high-performance liquid chromatography using an optically active column.

[Chem. 42]

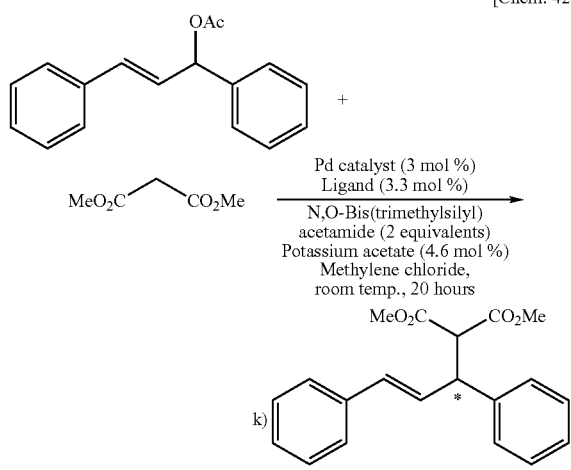

| Pd catalyst | Ligand | Yield | Enantiomer excess |
|---|---|---|---|
| [Pd(eta$^3$-C$_3$H$_5$)Cl]$_2$ | Compound 9 | 90% | 85% ee |
| Pd$_2$dba$_3$ • CHCl$_3$ | Compound 8 | 89% | 84% ee |

Embodiment 8

Asymmetric Allylic Amination

To a 20 mL flask were charged a palladium catalyst (0.03 mmol), ligand (0.033 mmol), and THF (3 mL) and the mixture was stirred for one hour. Benzyl amine and 1,3-diphenylpropenyl acetate were then added and the mixture was stirred for 16 hours at room temperature. Following ether extraction, the product was purified by column chromatography. The optical purity was determined by high-performance liquid chromatography using an optically active column.

[Chem. 43]

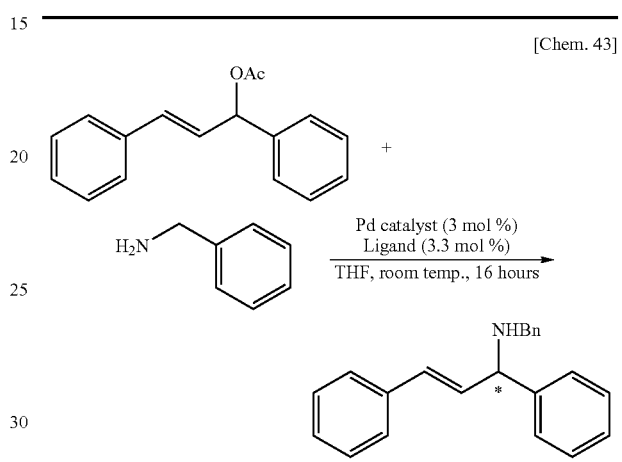

| Pd catalyst | Ligand | Yield | Enantiomer excess |
|---|---|---|---|
| [Pd(eta$^3$-C$_3$H$_5$)Cl]$_2$ | Compound 9 | 76% | 85% ee |
| Pd$_2$dba$_3$ • CHCl$_3$ | Compound 8 | 92% | 92% ee |

INDUSTRIAL APPLICABILITY

The present invention can be employed in the synthesis of a broad range of optically active aryl compounds and the like.

The invention claimed is:

1. A compound denoted by general formula (1a) or (1b) below:

[Chem. 1]

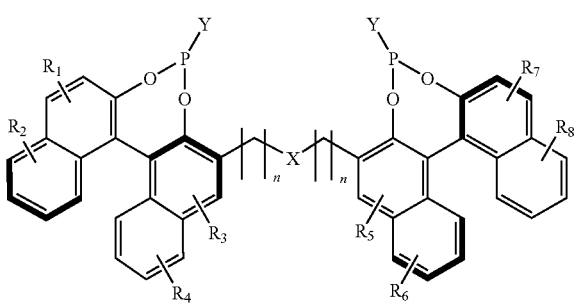

(1a)

-continued

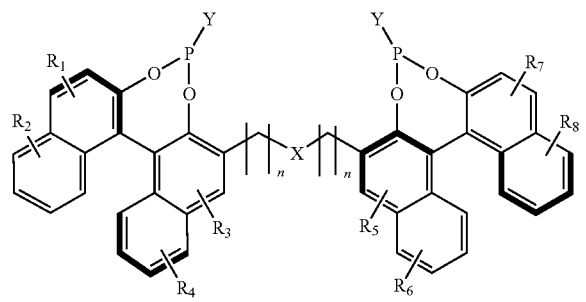

(1b)

(wherein X denotes carbon, oxygen, sulfur, or nitrogen; Y denotes $NR^{10}R^{11}$ (wherein $R^{10}$ and $R^{11}$ each independently denote a substituted or unsubstituted alkyl group, or a substituted or unsubstituted aryl group), $OR^{12}$ (wherein $R^{12}$ denotes a substituted or unsubstituted alkyl group, or substituted or unsubstituted aryl group), or $SR^{13}$ (wherein $R^{13}$ denotes a substituted or unsubstituted alkyl group, or a substituted or unsubstituted aryl group); n denotes an integer of from 1 to 3; $R^1$ to $R^8$ each independently denote hydrogen, a substituted or unsubstituted alkyl group, or a substituted or unsubstituted aryl group).

2. A complex, the core metal of which is rhodium, iridium, or ruthenium, comprising the compound denoted by general formula (1a) or (1b) of claim 1 as ligand.

3. The complex according to claim 2 denoted by general formula (20) below:

$$M^1X_mL^1_pL^2_q \qquad (20)$$

(wherein $M^1$ denotes rhodium, iridium, or ruthenium; X denotes a halogen, RO (wherein RO denotes a member selected from the group consisting of hydroxy, alkoxy, acetyl acetonate, acetoxy, and trifluoromethane sulfonate), a $BF_4$, $ClO_4$, $PF_6$, $B(Ar)_4$, or $SbF_6$ anion, or hydrogen; m denotes an integer of from 1 to 3; $L^1$ denotes an olefin, $eta^3$-allyl, aryl (Ar) group, amine, carbon monoxide, or acetonitrile; p denotes an integer of from 0 to 3; $L^2$ denotes the compound represented by general formula (1a) or (1b); q denotes the integer 1 or 2; and aryl (Ar) denotes an aromatic ring).

4. A catalyst for synthesizing optically active beta-substituted carbonyl compounds comprising the complexes according to claim 2.

5. A catalyst for asymmetric 1,2-addition reactions comprised of the complexes according to claim 2.

6. A method of manufacturing an optically active beta-substituted carbonyl compound by reacting a substituted or unsubstituted alpha, beta-unsaturated compound and an organic metal reagent, characterized by conducting the reaction in the presence of the complex according to claim 2.

7. The method according to claim 6, wherein the substituent in said alpha, beta-unsaturated compound is a carboxyl group, alkoxycarbonyl group, cyano group, substituted carbamoyl group, acyl group, formyl group, or nitro group.

8. The method according to claim 6, wherein said alpha, beta-unsaturated compound is a compound denoted by general formula (2a) or (2b) below:

[Chem. 2]

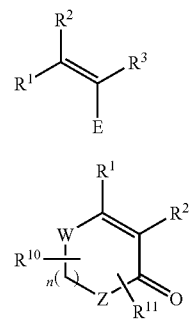

(2a)

(2b)

(wherein $R^1$, $R^2$, and $R^3$, which may be identical or different, each denote a hydrogen, alkyl group having 1 to 8 carbon atoms, alkoxy group having 1 to 8 carbon atoms, alkylthio group having 1 to 8 carbon atoms, or amino group optionally having an alkyl group with 1 to 8 carbon atoms; E denotes a carboxyl group, cyano group, carbamoyl group optionally having an alkyl group with 1 to 8 carbon atoms, or nitro group; n denotes an integer of 0 or greater; W and Z, which may be identical or different, each denote $—CH_2—$, $=CH—$, $—O—$, $—S—$, $—NH—$, or $=N—$; $R^{10}$ and $R^{11}$, which may be identical or different, each denote a hydrogen atom, alkyl group having 1 to 8 carbon atoms, alkoxy group having 1 to 8 carbon atoms, nitro group, cyano group, acyl group having 2 to 8 carbon atoms, alkoxycarbonyl group having 2 to 8 carbon atoms, or amino group optionally having an alkyl group with 1 to 8 carbon atoms, or adjacent $R^{10}$ and $R^{11}$ denote general formula (a) below:

[Chem. 3]

(a)

(wherein $R^{12}$ denotes a hydrogen atom, alkyl group having 1 to 8 carbon atoms, alkoxy group having 1 to 8 carbon atoms, cyano group, halogenated alkyl group, halogen atom, carbamoyl group optionally having an alkyl group with 1 to 8 carbon atoms, acyl group having 2 to 8 carbon atoms, alkoxycarbonyl group having 2 to 8 carbon atoms, or amino group optionally having an alkyl group with 1 to 8 carbon atoms)).

9. The method according to claim 6, wherein said organometallic reagent is a metal-substituted or unsubstituted alkyl, alkenyl, alkynyl, or aryl compound.

10. The method according to claim 6, wherein said organometallic reagent is an organic boronic acid derivative of the compound denoted by general formula (3a), (3b), or (3c):

[Chem. 4]

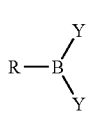

(3a)

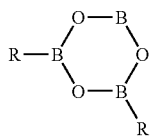
(3b)

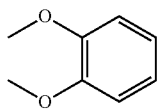
(3c)

(wherein Y denotes a hydroxyl group, alkoxy group having 1 to 8 carbon atoms, phenoxy group optionally having an alkyl group with 1 to 8 carbon atoms, cyclohexyloxy group, or group denoted by formula a, b, c, or d (in each of which q denotes an integer of from 1 to 4; r and s each independently denote an integer of from 0 to 5, and Me denotes a methyl group); and R denotes a substituted or unsubstituted alkyl, alkenyl, alkynyl, or aryl group).

[Chem. 5]

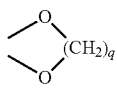 a

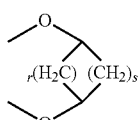 b

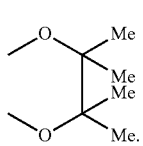 c

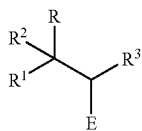 d

11. The method according to claim 6, wherein said optically active beta-substituted carbonyl compound denotes the compound represented by general formula (4) below:

[Chem. 6]

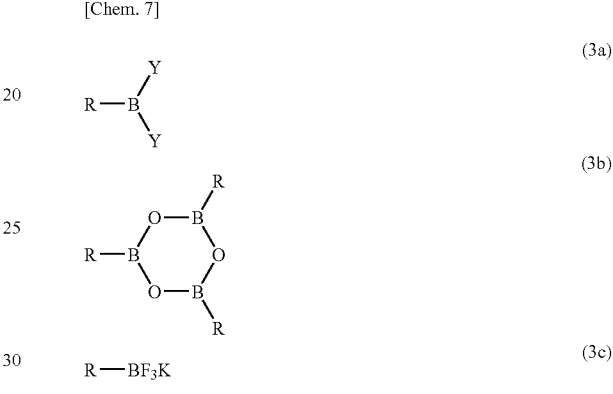

(wherein $R^1$, $R^2$, and $R^3$, which may be identical or different, each denote a hydrogen atom, alkyl group having 1 to 8 carbon atoms, alkoxy group having 1 to 8 carbon atoms, alkylthio group having 1 to 8 carbon atoms, or amino group optionally having an alkyl group with 1 to 8 carbon atoms; E denotes a carboxyl group, cyano group, carbamoyl group optionally having an alkyl group with 1 to 8 carbon atoms, or nitro group; and R denotes a substituted or unsubstituted alkyl, alkenyl, alkynyl, or aryl group).

12. A method of manufacturing an optically active alcohol compound by reacting an aldehyde compound and an organometallic reagent, characterized by being conducted in the presence of the complex according to claim 2.

13. The method according to claim 12, wherein said aldehyde compound is the compound denoted by general formula (5):

$$R^4CHO \qquad (5)$$

(wherein $R^4$ denotes a substituted or unsubstituted alkyl group or substituted or unsubstituted aryl group).

14. The method according to claim 12, wherein said organometallic reagent is a metal-substituted or unsubstituted alkyl, alkenyl, alkynyl, or aryl group.

15. The method according to claim 12, wherein said organometallic reagent is an organoboronic acid derivative denoted by general formula (3a), (3b), or (3c) below:

[Chem. 7]

(wherein Y denotes a hydroxyl group, alkoxy group having 1 to 8 carbon atoms, phenoxy group optionally having an alkyl group with 1 to 8 carbon atoms, cyclohexyloxy group, or the group denoted by formula a, b, c, or d below (in each of which q denotes an integer of from 1 to 4, r and s each independently denote an integer of from 0 to 5, and Me denotes a methyl group); and R denotes a substituted or unsubstituted alkyl, alkenyl, alkynyl, or aryl group):

[Chem.8]

16. The method according to claim 12, wherein said optically active alcohol is the compound denoted by general formula (7) below:

[Chem. 9]

(7)

(wherein $R^4$ denotes a substituted or unsubstituted alkyl group or a substituted or unsubstituted aryl group; and R denotes a substituted or unsubstituted alkyl, alkenyl, alkynyl, or aryl group).

17. A complex, the core metal of which is palladium or platinum, comprising the compound denoted by general formula (1a) or (1b) of claim 1 as ligand.

18. The complex according to claim 17, denoted by general formula (21) below:

$$M^2X_rL^3{}_sL^4{}_t \qquad (21)$$

(wherein $M^2$ denotes palladium or platinum; X denotes a halogen, acetate anion, $BF_4$, $PF_6$, $ClO_4$, $B(Ar)_4$, or $SbF_6$ anion; r denotes an integer of from 0 to 2; $L^3$ denotes a triaryl (or alkyl) phosphine, acetonitrile, benzonitrile, dibenzylidene acetone, or eta$^3$-allyl; s denotes an integer of from 0 to 2; $L^4$ denotes the compound according to general formula (1a) or (1b); t denotes 1; and Ar denotes an aromatic ring).

19. A catalyst for an asymmetric allylic substitution reaction, comprising the complex according to claim 17.

20. The catalyst according to claim 19, in which the asymmetric allylic substitution reaction is an asymmetric allylic alkylation reaction.

21. The catalyst according to claim 19, wherein the asymmetric allylic substitution reaction is an asymmetric allylic amination reaction.

22. A method of manufacturing an optically active (1,3-disubstituted propenyl)dialkyl malonate compound by reacting a 1,3-disubstituted allyl acetate compound with a dialkyl malonate, characterized by conducting said reaction in the presence of the complex according to claim 17.

23. The method according to claim 22, wherein said 1,3-disubstituted allyl acetate compound is the compound denoted by general formula (8) below:

[Chem. 10]

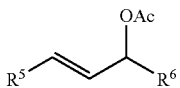
(8)

(wherein $R^5$ and $R^6$ denote identical substituted or unsubstituted alkyl groups, or substituted or unsubstituted aryl groups; and Ac denotes an acetyl group).

24. The method according to claim 22, wherein said dialkyl malonate is the compound dented by general formula (9) below:

[Chem. 11]

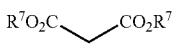
(9)

(wherein $R^7$ denotes a substituted or unsubstituted alkyl group).

25. The method according to claim 22, wherein said optically active (1,3-disubstituted propenyl)dialkyl malonate compound is the compound denoted by general formula (10) below:

[Chem. 12]

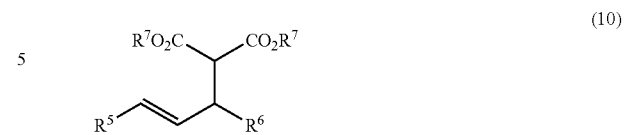
(10)

(wherein $R^5$ and $R^6$ denote identical substituted or unsubstituted alkyl groups or substituted or unsubstituted aryl groups; and $R^7$ denotes a substituted or unsubstituted alkyl group).

26. A method of manufacturing an optically active allylamine compound by reacting a 1,3-disubstituted allyl acetate compound and an amine compound, characterized by conducting said reaction in the presence of the complex according to claim 17.

27. The method according to claim 26, wherein said 1,3-disubstituted allyl acetate compound is the compound denoted by general formula (11) below:

[Chem. 13]

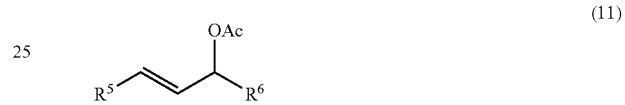
(11)

(wherein $R^5$ and $R^6$ denote identical substituted or unsubstituted alkyl groups or substituted or unsubstituted aryl groups; and Ac denotes an acetyl group).

28. The method according to claim 26, wherein said amine compound is the compound denoted by general formula (12) below:

[Chem. 14]

(12)

(wherein $R^8$ and $R^9$ each independently denote hydrogen, a substituted or unsubstituted alkyl group, or a substituted or unsubstituted aryl group, it being permissible for $R^8$ and $R^9$ to form a ring having 3 to 7 carbon atoms).

29. The method according to claim 26, wherein said optically active allylamine compound is the compound denoted by general formula (13) below:

[Chem. 15]

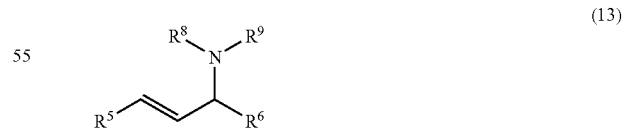
(13)

(wherein $R^5$ and $R^6$ denote identical substituted or unsubstituted alkyl groups or substituted or unsubstituted aryl groups; and $R^8$ and $R^9$ each independently denote hydrogen, a substituted or unsubstituted alkyl group, or a substituted or unsubstituted aryl group, it being permissible for $R^8$ and $R^9$ to form a ring having 3 to 7 carbon atoms).

\* \* \* \* \*